(12) United States Patent
Levine et al.

(10) Patent No.: US 7,655,752 B2
(45) Date of Patent: Feb. 2, 2010

(54) TNF-α CONVERTING ENZYME INHIBITORY AGENTS AND METHOD OF USING SAME

(75) Inventors: Stewart J. Levine, North Potomac, MD (US); Caitriona A. Buckley, Potomac, MD (US); Farshid N. Rouhani, Germantown, MD (US); Maryann Kaler, Bethesda, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 157 days.

(21) Appl. No.: 11/389,675

(22) Filed: Mar. 24, 2006

(65) Prior Publication Data

US 2007/0004007 A1    Jan. 4, 2007

Related U.S. Application Data

(63) Continuation of application No. PCT/US2004/031608, filed on Sep. 24, 2004.

(60) Provisional application No. 60/505,394, filed on Sep. 24, 2003.

(51) Int. Cl.
| | |
|---|---|
| *A61K 38/00* | (2006.01) |
| *C07L 2/00* | (2006.01) |
| *C07K 4/00* | (2006.01) |
| *C07K 5/00* | (2006.01) |
| *C07K 7/00* | (2006.01) |
| *C07K 14/00* | (2006.01) |
| *C07K 16/00* | (2006.01) |
| *C07K 17/00* | (2006.01) |

(52) U.S. Cl. .......................... 530/300; 514/12; 514/13; 514/16

(58) Field of Classification Search .................. None
See application file for complete search history.

(56) References Cited

U.S. PATENT DOCUMENTS 6,406,901 B1 * 6/2002 Black et al. ................ 435/219
6,932,971 B2 * 8/2005 Bachmann et al. ....... 424/193.1

FOREIGN PATENT DOCUMENTS

| WO | WO-9641624 A1 | | 12/1996 |
|---|---|---|---|
| WO | WO 99/06549 | * | 2/1999 |
| WO | WO-2005030798 A2 | | 4/2005 |
| WO | WO-2005030798 A3 | | 4/2005 |

OTHER PUBLICATIONS

"Adam 17 Precursor (EC 3.4.24.86) (A Disintegrin and Metalloproteinase Domain 17) (TNF- Alpha Converting Enzyme) (TNF - Alpha Convertase) (Snake Venom-like Protease) (CD156b Antigen)", *Database Uniprot Online*, Retrieved from EBI Accession No. UNIPROT: P78536, Database Accession No. P78536,(Oct. 16, 2001).

Lee, M-H. , et al., "Mapping and Characterization of the Functional Epitopes of Tissue Inhibitor of Metalloproteinases(TIMP)-3 using TIMP-1 as the Scaffold: A New Frontier in TIMP Engineering", *Protein Sceince*, 11(10), ISSN: 0961-8368,(Oct. 2002),2493-2503.

Lee, M-H. , et al., "The C-Terminal Domains of TACE weaken the Inhibitory Action of N-TIMP-3", 520 (1-3), FEBS Letter, Elsevier Science Publishers,ISSN:0014-5793,(Jun. 5, 2002),102-106.

Maskos, K. , et al., "Crystal Structure of the Catalytic Domain of Human Tumor Necrosis Factor-alpha-Converting Enzyme", *Proceedings of the National Academy of Sciences*, 95 (7), ISSN: 0027-8424, Mar. 31, 1998),3408-3412.

Milla, M. E., et al., "Specific Sequence Elements are Required for the Expression of Functional Tumor Necrosis Factor-alpha-Converting Enzyme(TACE)", *Journal of Biology Chemistry*, 274 (43), ISSN: 0021-9258,(Oct. 22, 1999),30563-30570.

* cited by examiner

*Primary Examiner*—Robert Landsman
(74) *Attorney, Agent, or Firm*—Sheridan Ross P.C.

(57) ABSTRACT

The invention provides peptides, variants of peptides, peptide fragments, and peptidomimetics that can inhibit the protease activity of tumor necrosis factor alpha converting enzyme. The invention also provides coupled proteins containing a partner protein coupled to a peptide, peptide fragment, or peptidomimetic. The invention also provides polyproteins containing at least two peptides, peptide fragments, or coupled proteins that are connected through a linker. Isolated nucleic acid segments, expression cassettes, and nucleic acid constructs are also provided by the invention. The invention also provides antibodies and aptamers. Pharmaceutical compositions are provided by the invention. Methods to lower or increase levels of active tumor necrosis factor alpha in a mammal are also provided.

18 Claims, 14 Drawing Sheets

Fig. 1C

SEQUENCE LISTING

```
<160> NUMBER OF SEQ ID NOS: 13

<210> SEQ ID NO 1
<211> LENGTH: 6
<212> TYPE: PRT
<213> ORGANISM: Homo sapiens

<400> SEQUENCE: 1

Ile Glu Gly Arg Met Asp
 1               5

<210> SEQ ID NO 2
<211> LENGTH: 6
<212> TYPE: PRT
<213> ORGANISM: Homo sapiens

<400> SEQUENCE: 2

Pro Lys Val Cys Gly Tyr
 1               5

<210> SEQ ID NO 3
<211> LENGTH: 54
<212> TYPE: PRT
<213> ORGANISM: Homo sapiens

<400> SEQUENCE: 3

Met Arg Gln Ser Leu Leu Phe Leu Thr Ser Val Val Pro Phe Val Leu
 1               5                  10                  15

Ala Pro Arg Pro Pro Asp Asp Pro Gly Phe Gly Pro His Gln Arg Leu
                20                  25                  30

Glu Lys Leu Asp Ser Leu Leu Ser Asp Tyr Asp Ile Leu Ser Leu Ser
            35                  40                  45

Asn Ile Gln Gln His Ser
    50

<210> SEQ ID NO 4
<211> LENGTH: 19
```

```
<212> TYPE: PRT
<213> ORGANISM: Homo sapiens

<400> SEQUENCE: 4

Gln Arg Leu Glu Lys Leu Asp Ser Leu Ser Asp Tyr Asp Ile Leu
 1               5                  10                  15
Ser Leu Ser

<210> SEQ ID NO 5
<211> LENGTH: 17
<212> TYPE: PRT
<213> ORGANISM: Homo sapiens

<400> SEQUENCE: 5

Arg Leu Glu Lys Leu Asp Ser Leu Leu Ser Asp Tyr Asp Ile Leu Ser
 1               5                  10                  15
Leu

<210> SEQ ID NO 6
<211> LENGTH: 7
<212> TYPE: PRT
<213> ORGANISM: Homo sapiens

<400> SEQUENCE: 6

Val Leu Ala Pro Arg Pro Pro
 1               5

<210> SEQ ID NO 7
<211> LENGTH: 24
<212> TYPE: PRT
<213> ORGANISM: Homo sapiens

<400> SEQUENCE: 7

Arg Leu Glu Lys Leu Asp Ser Leu Leu Ser Asp Tyr Asp Ile Leu Ser
 1               5                  10                  15
Leu Ser Asn Ile Gln Gln His Ser
                20

<210> SEQ ID NO 8
<211> LENGTH: 37
<212> TYPE: PRT
<213> ORGANISM: Homo sapiens

<400> SEQUENCE: 8

Pro Arg Pro Pro Asp Asp Pro Gly Phe Gly Pro His Gln Arg Leu Glu
 1               5                  10                  15
Lys Leu Asp Ser Leu Leu Ser Asp Tyr Asp Ile Leu Ser Leu Ser Asn
                20                  25                  30
Ile Gln Gln His Ser
        35

<210> SEQ ID NO 9
<211> LENGTH: 6
<212> TYPE: PRT
<213> ORGANISM: Homo sapiens

<400> SEQUENCE: 9

Pro Lys Thr Cys Gly Tyr
 1               5

<210> SEQ ID NO 10
<211> LENGTH: 165
```

-continued

```
<212> TYPE: DNA
<213> ORGANISM: Homo sapiens

<400> SEQUENCE: 10
atgaggcagt ctctcctatt cctgaccagc gtggttcctt tcgtgctggc gccgcgacct      60
ccggatgacc cgggcttcgg cccccaccag agactcgaga agcttgattc tttgctctca     120
gactacgata ttctctcttt atctaatatc cagcagcatt cgtaa                     165

<210> SEQ ID NO 11
<211> LENGTH: 21
<212> TYPE: DNA
<213> ORGANISM: Homo sapiens

<400> SEQUENCE: 11
cgggaacatg aggcagtctc t                                                21

<210> SEQ ID NO 12
<211> LENGTH: 21
<212> TYPE: DNA
<213> ORGANISM: Homo sapiens

<400> SEQUENCE: 12
gcactctgtt tctttgctgt t                                                21

<210> SEQ ID NO 13
<211> LENGTH: 509
<212> TYPE: DNA
<213> ORGANISM: Homo sapiens

<400> SEQUENCE: 13
cgggaacatg aggcagtctc tcctattcct gaccagcgtg gttcctttcg tgctggcgcc      60
gcgacctccg gatgacccgg gcttcggccc caccagaga ctcgagaagc ttgattcttt     120
gctctcagac tacgatattc tctctttatc taatatccag cagcattcgt aacgtcgaaa    180
tgctgagcag catggattct gcatcggttc gcattatcaa acccttttcct gcgccccaga   240 ctccaggccg cctgcagcct gcccctgtga tcccttcggc gccagcagct ccaaaactgg    300
accaccagag aatggacacc atccaggaag accccagcac agactcacat atggacgagg    360
atgggtttga aaggacccc ttcccaaata gcagcacagc tgccaagtca tttgaggatc     420
tcacggacca tccggtcacc agaagtgaaa aggctgcctc ctttaaactg cagcgtcaga    480
atcgtgttaa cagcaaagaa acagagtgc                                      509
```

TNF-α CONVERTING ENZYME INHIBITORY AGENTS AND METHOD OF USING SAME

CLAIM OF PRIORITY

This application is a continuation under 35 U.S.C. 111(a) of PCT/US2004/031608, filed Sep. 24, 2004 and published as WO 2005/030798 A2, filed Apr. 7, 2005, which claimed priority under 35 U.S.C. 119(e) to U.S. Provisional Patent Application No. 60/505,394, filed Sep. 24, 2003, which applications and publication are incorporated herein by reference and made a part hereof.

GOVERNMENT FUNDING

The invention described herein was developed with the support of the Department of Health and Human Services. The United States Government has certain rights in the invention.

FIELD OF THE INVENTION

The invention relates to the field of metalloproteases. Specifically, the invention relates to activation or inhibition of the ADAM family of proteases. More specifically, the invention relates to activation or inhibition of the TNF-α converting enzyme (TACE).

BACKGROUND OF THE INVENTION

Tumor necrosis factor alpha (TNF-α) converting enzyme (TACE) or ADAM 17 (a disintegrin and metalloprotease), a member of a family of zinc metalloproteases, is an important regulator of inflammation, immune regulation, and cellular proliferation as a consequence of its ability to process integral cell surface proteins to soluble forms (Moss et al., *Drug Discov. Today*, 6:417 (2001); Black, *Int. J. Biochem. Cell. Biol.*, 34:1 (2002); Moss et al., *Cell*, 90:589 (1997)). TACE was originally identified as the enzyme that cleaves the membrane-bound precursor of tumor necrosis factor-alpha (TNF-α) (Moss et al., *Drug Discov. Today*, 6:417 (2001); Moss et al., *Nature*, 385:733 (1997); Black et al., *Nature*, 385:729 (1997)). Other cell surface proteins that have been identified as substrates for TACE include L-selectin (Peschon et al., *Science* 282:1281 (1998)), transforming growth factor-α, TNF receptors I and II (Peschon et al., *Science*, 282:1281 (1998); Reddy et al., *J. Biol. Chem.*, 275:14608 (2000)), interleukin-6 receptor-α (Althoff et al., *Eur. J. Biochem.*, 267:2624 (2000)), interleukin-1 receptor II (Reddy et al., *J. Biol. Chem.*, 275:14608 (2000)), Notch1 receptor (Brou et al., *Mol. Cell.*, 5:207 (2000)), TNF-related activation-induced cytokine (TRANCE) (Schlondorff et al., *J. Biol. Chem.*, 276:14665 (2001)), amyloid precursor protein (Buxbaum et al., *J. Biol. Chem.*, 273:27765 (1998)), fractalkine (CX3CL1) (Garton et al., *J. Biol. Chem.*, 276:37993 (2001)), CD30 (Hansen et al., *J. Immunol.*, 165:6703 (2000)), CD40 (Contin et al., *J. Biol. Chem.*, (2003)), macrophage colony stimulating factor receptor (Rovida et al., *J. Immunol.*, 166:1583 (2001)), cellular prion protein (Vincent et al., *J. Biol. Chem.*, 276:37743 (2001)), MUC1 (Thethiah et al., *J. Biol. Chem.*, 278:3386 (2003)), growth hormone binding protein (Zhang et al., *Endocrinology* 141:4342 (2000)), erbB4/HER4 (Rio et al., *J. Biol. Chem.*, 275:10379 (2000)), pro-heparin binding EGF-like growth factor (Merlos-Suarez et al., *J. Biol. Chem.*, 276:48510 (2001)), and amphiregulin (Sunnarborg et al., *J. Biol. Chem.*, 277:12838 (2002)).

ADAM family zinc metalloproteases, including TACE, typically have a conserved structure that includes a signal sequence, prodomain, metalloprotease domain, disintegrin domain, cysteine-rich domain containing an epidermal growth factor-like repeat, a transmembrane domain and an intracytoplasmic tail (Moss et al., *Drug Discov. Today*, 6:417 (2001); Moss et al., *Nature*, 385:733 (1997); Black et al., *Nature*, 385:729 (1997); Schlondorff et al., *Biochem. J.*, 347:131 (2000); Schlondorff and Blobel, *J. Cell. Sci.*, 112:3603 (1999)). The function of the prodomain is to retain the proenzyme in an inactive state via a cysteine switch mechanism, whereby a cysteine in the prodomain coordinates with a zinc molecule in the catalytic site (Van Wart and Birkedal-Hansen, *Proc. Natl. Acad. Sci. USA*, 87:5578 (1990)). The TACE prodomain may also play an important role in protein folding, as TACE mutants lacking the prodomain are inefficiently synthesized in insect cells, suggesting intracellular degradation (Milla et al., *J. Biol. Chem.*, 274:30563 (1999)). Removal of the TACE prodomain occurs in the late Golgi compartment and can be mediated by furin and other proprotein-convertases, such as PC7 (Schlondorff et al., *Biochem. J.*, 347:131 (2000); Endres et al., *Eur. J. Biochem.*, 270:2386 (2003); Borroto et al., *J. Biol. Chem.*, 278:25933 (2003); Peiretti et al., *Exp. Cell. Res.*, 285:278 (2003)). Mutant cell lines with impaired intracellular trafficking of TACE to the Golgi compartment have been described (Borroto et al., *J. Biol. Chem.*, 278:25933 (2003)). These cells accumulate full-length, inactive protein within the endoplasmic reticulum and demonstrate a gross defect in ectodomain shedding. Stimulation with phorbol ester, a potent inducer of cell surface shedding, induces internalization and degradation of TACE from the plasma membrane and impairs TACE prodomain cleavage and maturation (Endres et al., *Eur. J. Biochem.*, 270:2386 (2003); Doedens et al., *J. Biol. Chem.*, 275:14598 (2000)).

The action of TNF-α has been implicated in such diseases as arthritis, sepsis, ulcerative colitis, multiple sclerosis, Crohn's disease, septic shock, graft rejection, cachexia, insulin resistance, post-ischemic reperfusion injury, tumor metastasis, tissue ulceration, abnormal wound healing, periodontal disease, bone disease, proteinuria, aneurysmal aortic disease, degenerative cartilage loss, demyelinating diseases of the nervous system, and HIV infection. Accordingly, agents, compositions, and methods that can be used to increase or decrease the activity of TNF-α converting enzyme are needed.

SUMMARY OF THE INVENTION

These needs are met by the invention described herein. The invention provides peptides, variants of peptides, peptide fragments, and peptidomimetics that can inhibit the protease activity of tumor necrosis factor alpha converting enzyme. The invention also provides coupled proteins containing a partner protein coupled to a peptide, peptide fragment, or peptidomimetic. The invention also provides polyproteins containing at least two peptides or peptide fragments that are connected through a linker. Isolated nucleic acid segments, expression cassettes, and nucleic acid constructs are also provided by the invention. The invention also provides antibodies and aptamers. Pharmaceutical compositions are provided by the invention. Methods to lower or increase levels of active tumor necrosis factor alpha in a mammal are also provided.

The invention provides isolated peptides. The isolated peptides can be variants of the amino acid sequence as put forth in SEQ ID NO:3. Preferably the peptide includes an amino-terminal blocker. More preferably the peptide includes a carboxyl-terminal blocker. Most preferably the peptide includes an amino-terminal blocker and a carboxyl-terminal blocker. The isolated peptide can have an amino acid deletion. Preferably the isolated peptide has a one amino acid deletion. More preferably the isolated peptide has a five amino acid deletion. Most preferably the isolated peptide has a ten amino acid deletion. The isolated peptide can include an amino acid addition. Preferably the isolated peptide has a one amino acid addition. More preferably the isolated peptide has a five amino acid addition. Most preferably the isolated peptide has a ten amino acid addition. The isolated peptide can include an amino acid substitution. Preferably the amino acid substitution is a conservative amino acid substitution. Preferably the isolated peptide has the amino acid sequence as put forth in SEQ ID NO:3.

The invention provides peptide fragments of SEQ ID NO:3 that inhibit the protease activity of TACE. Preferably the peptide fragments include at least five amino acids. More preferably the peptide fragments include at least ten amino acids. Even more preferably the peptide fragments include at least fifteen amino acids. Most preferably the peptide fragments include at least twenty amino acids. Preferably the peptide fragment includes an amino-terminal blocker. More preferably the peptide fragment includes a carboxyl-terminal blocker. Most preferably the peptide fragment includes an amino-terminal blocker and a carboxyl-terminal blocker. The isolated peptide fragment can include an amino acid substitution. Preferably the amino acid substitution is a conservative amino acid substitution.

The invention provides peptidomimetics that inhibit the protease activity of TACE. Preferably the peptidomimetic includes an amino-terminal blocker. More preferably the peptidomimetic includes a carboxyl-terminal blocker. Most preferably the peptidomimetic includes an amino-terminal blocker and a carboxyl-terminal blocker.

The invention provides coupled proteins that include a partner protein coupled to a peptide, a peptide fragment, or a peptidomimetic as provided by the invention. Preferably the partner protein is chemically coupled to a peptide, a peptide fragment, or a peptidomimetic of the invention. More preferably the partner protein is coupled to a peptide or peptide fragment through expression of a fusion protein. Preferably the partner protein is an export signal. More preferably the partner protein is a carrier protein that increases the immunogenicity of the coupled protein.

The invention provides polyproteins that include at least two peptides, at least two peptide fragments, at least two coupled proteins, or combinations thereof, that are connected by a linker. The polyprotein may be connected to a partner protein by a linker. Preferably the linker is an amino acid sequence that is cleavable to release the partner protein, peptides, peptide fragments, and coupled proteins of the invention. Preferably the linker is cleavable with a chemical. More preferably the linker is cleavable with a protease. Preferably a polyprotein includes at least two copies of a peptide, peptide fragment, or coupled protein of the invention. More preferably a polyprotein includes at least five copies of a peptide, peptide fragment, or coupled protein of the invention. Even more preferably a polyprotein includes at least ten copies of a peptide, peptide fragment, or coupled protein of the invention. Most preferably a polyprotein includes at least twenty copies of a peptide, peptide fragment, or coupled protein of the invention. Preferably the partner protein connected to the polyprotein is an antibody epitope. More preferably the partner protein connected to the polyprotein is avidin. Still more preferably the partner protein connected to the polyprotein is biotin. Even still more preferably the partner protein connected to the polyprotein is poly histidine. Yet even still more preferably the partner protein connected to the polyprotein is glutathione-S-transferase. Most preferably the partner protein connected to the polyprotein is maltose binding protein.

The invention provides an isolated nucleic acid segment that encodes an amino acid sequence according to SEQ ID NO:3. The invention also provides isolated nucleic acid segments that encode peptide fragments of SEQ ID NO:3 that inhibit the protease activity of TACE. Preferably the nucleic acid segments are ribonucleic acid. More preferably the nucleic acid segments are deoxyribonucleic acid.

The invention provides an expression cassette that includes a regulatory sequence operably linked to a nucleic acid segment of the invention. Preferably the regulatory sequence is an enhancer. More preferably the regulatory sequence is an intron. Even more preferably the regulatory sequence is a polyadenylation signal sequence. Still even more preferably the regulatory sequence is a repressor binding site. Yet still even more preferably the regulatory sequence is a translation leader sequence. Most preferably the regulatory sequence is a promoter.

The invention provides a nucleic acid construct that includes a nucleic acid segment of the invention and a vector. Preferably the vector is a bacteriophage. More preferably the vector is a virus. Even more preferably the vector is a phagemid. Still even more preferably the vector is a cosmid. Most preferably the vector is a plasmid.

The invention provides an antibody that binds to an amino acid sequence according to SEQ ID NO:3. Preferably the antibody selectively binds to an amino acid sequence according to SEQ ID NO:3. Preferably the antibody is a polyclonal antibody. More preferably the antibody is an antibody fragment. Even more preferably the antibody is a single-chain antibody. Still even more preferably the antibody is a humanized antibody. Most preferably the antibody is a monoclonal antibody. Preferably the antibody will bind to a peptide having SEQ ID NO:3 and thereby increase the activity of tumor necrosis factor alpha converting enzyme.

The invention provides an aptamer that binds to an amino acid sequence according to SEQ ID NO:3. Preferably the aptamer will bind to a peptide having SEQ ID NO:3 and thereby increase the activity of tumor necrosis factor alpha converting enzyme.

The invention provides a pharmaceutical composition comprising a pharmaceutical carrier and a peptide, peptide fragment, peptidomimetic, polyprotein, antibody, or aptamer of the invention, or combinations thereof. Preferably the pharmaceutical composition is packaged in unit dosage form.

The invention provides a method to lower levels of tumor necrosis factor alpha in a mammal that involves administering a tumor necrosis factor lowering amount of a peptide, peptide fragment, peptidomimetic, coupled protein, or polyprotein of the invention to the mammal. Preferably the peptide, peptide fragment, peptidomimetic, coupled protein, or polyprotein of the invention is formulated as a pharmaceutical composition. Preferably the method is used to reduce or eliminate a growth hormone related disease. More preferably the method is used to reduce or eliminate a cellular proliferation. Still more preferably the method is used to reduce or eliminate metastasis of tumor cells. Most preferably the method is used to reduce or eliminate inflammation. Preferably the inflammatory disease is inflammatory bowel disease. More preferably the inflammatory disease is pleurisy. Still more preferably the inflammatory disease is physical injury. Even still more preferably the inflammatory disease is lipopolysaccharide-induced septic shock. Most preferably the inflammatory disease is arthritis. Preferably the mammal is a cat. More preferably the mammal is a dog. Even more preferably the mammal is a horse. Most preferably the mammal is a human.

The invention provides a method to increase levels of tumor necrosis factor alpha in a mammal that involves administering a tumor necrosis factor increasing amount of an antibody or aptamer of the invention to the mammal. Preferably the antibody or aptamer of the invention is formulated as a pharmaceutical composition. Preferably the method is used to reduce or eliminate a growth hormone related disease. More preferably the method is used to reduce or eliminate Alzheimer's disease. Most preferably the method is used to induce apoptosis of cancer cells. Preferably the mammal is a cat. More preferably the mammal is a dog. Even more preferably the mammal is a horse. Most preferably the mammal is a human.

BRIEF DESCRIPTION OF THE FIGURES

FIG. 1C shows the nucleotide and amino acid sequences of N-TACE. The 509 bp N-TACE cDNA (SEQ ID NO:13) encodes a 54 amino acid (SEQ ID NO: 3) protein that corresponds to the TACE signal sequence (single underlined) and the first 37 amino acids of the TACE prodomain. The 19 amino acid, leucine-rich inhibitory domain is denoted by the double underline. The stop codon is indicated by a star.

FIG. 2A shows a silver stained SDS-PAGE gel of rhTACE (0.5 µM) that was incubated with rhTNFR1:Fc (0.95 µM) alone or in combination with N-TACE(18-54) (80 µM) for 30 minutes. FIG. 2B shows a silver stained SDS-PAGE gel of rhTACE (0.5 µM) that was incubated with rhTNFR2:Fc (0.95 µM) alone or in combination with N-TACE(18-54) (80 µM) for 30 minutes. The position TNFR2:Fc cleavage products are indicated by arrows. FIG. 2C illustrates the structure of the TNFR1:Fc chimeric substrate which includes the entire extracellular domain of human TNFR1 (Met 1-Thr 211) (Schall et al., *Cell*, 61:361 (1990)) fused to the Fc region of human IgG1 (Pro 100-Lys 330) via a linker peptide (IEGRMD) (SEQ ID NO:1). FIG. 2D illustrates the structure of the TNFR2:Fc chimeric substrate which includes the entire extracellular domain of human TNFR2 (met 1-Asp 257) (Smith et al., *Science*, 248:1019 (1990); Kohno et al., *Proc. Natl. Acad. Sci. USA*, 87:8331 (1990)) fused to the Fc region of human IgG1 (Pro 100-Lys 330) via a linker peptide (IEGRMD) (SEQ ID NO:1). Both chimeric fusion proteins contain a 6X histidine tag at the carboxy-terminus. Molecular weight markers are indicated on the left.

FIG. 3A shows analysis of the samples by SDS-PAGE and silver staining. FIG. 3B shows analysis of the samples by immunoblotting with an antibody directed against the carboxy-terminal 6× histidine tag of TNFR2:Fc. The position of TNFR2:Fc, TACE, and TNFR2:Fc cleavage products are indicated by arrows. Molecular weight markers are indicated on the left.

DETAILED DESCRIPTION OF THE INVENTION

Figure 1A:
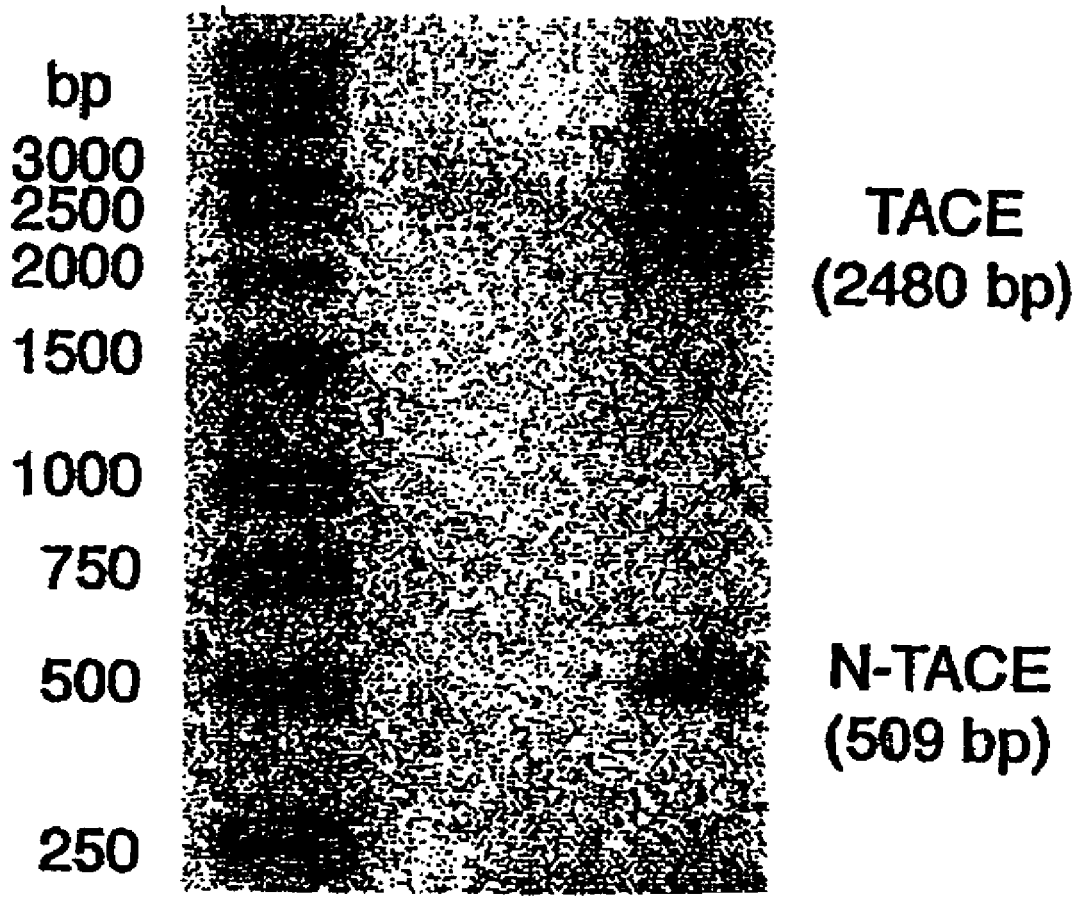
FIG. 1A illustrates a photonegative image of an SYBR Green stained agarose gel. The image shows the positions of the 2480 base pair TACE cDNA product, and the 509 base pair N-TACE cDNA product, that resulted from RT-PCR of total RNA isolated from NCI-H292 cells. Molecular weight markers are shown for comparison.

The invention provides agents that are inhibitors of TNF-α converting enzyme (TACE) activity. The invention also provides agents that are thought to be stimulators of TACE activity. These inhibitors are thought to act in a manner that is independent of a cysteine-switch mechanism.

Regulation of TNF-α converting enzyme (TACE) activity is important to prevent excessive or unanticipated cleavage and shedding of target membrane proteins. TACE is synthesized as a latent pro-enzyme, whereby the prodomain inhibits the catalytic site by a cysteine-switch mechanism.

The present invention is based on the discovery that the amino-terminus of the TACE prodomain possesses TACE inhibitory activity that is independent of a cysteine-switch mechanism. In addition, an endogenous mRNA sequence has been discovered that encodes a putative soluble protein corresponding to the initial 54 amino acids of full-length TACE. This protein has been named N-TACE and includes the signal peptide, but did not include the cysteine-switch motif (PKVCGY[186]) (SEQ ID NO:2) that is contained in the full length TACE protein.

According to the invention, the 54 amino acid peptide (N-TACE) was shown to inhibit TACE-mediated cleavage of a model protein substrate that contained a 75-kDa type II tumor necrosis factor receptor fused to an immunoglobulin constant region (TNFR2:Fc). According to the invention, a 19-amino acid, leucine-rich peptide having an amino acid sequence that corresponded to amino acids 30-48 of TACE (N-TACE(30-48)) was also able to inhibit the TACE-mediated cleavage of the TNFR2:Fc model protein substrate. To further characterize the function of N-TACE, a protein was synthesized which included N-TACE amino acids 18 to 54 (N-TACE(18-54)), but which did not include the signal peptide. N-TACE(18-54) inhibited TACE-mediated cleavage of a type II tumor necrosis factor receptor (TNFR2) in vitro. This inhibitory activity was specific, as neither vasoactive intestinal peptide (VIP) nor α-defensin possessed TACE inhibitory activity.

The ability of N-TACE to inhibit TACE activity was also tested in a cell-based system according to the invention. N-TACE was able to inhibit TACE catalytic activity. N-TACE (18-54) was also able to attenuate TNFR2 shedding by 42% when tested in a cell-based system using U937 monocytic cells. The results of the invention demonstrate the ability of peptides having amino acid sequences that correspond to that of TACE to inhibit cell-associated TACE.

The N-TACE concentrations used according to the invention to inhibit TACE were similar to the concentrations of other metalloprotease inhibitors that are effective against TACE. For example, in a cell-based assay, N-TACE(18-54) exhibited inhibitory effects at concentrations of 0.4 to 40 μM. This concentration is similar to the effective concentration of known TACE inhibitors. For example, TAPI-2, a hydroxamic acid based zinc metalloprotease inhibitor, is commonly utilized at a concentration of 10 to 100 μM to inhibit TACE (Zhang et al., *FASEB. J.*, 15:303 (2001); Zhang et al., *J. Biol. Chem.*, 275:15839 (2000); Slack et al., *Biochem. J.*, 357:787 (2001)). Similarly, GM6001, a broad-spectrum metalloprotease inhibitor, has been utilized in a range from 0.3 to 30 μM.

According to the invention, this discovery represents a novel cysteine-switch independent-mechanism by which the catalytic activity of TACE and other disintegrin metalloproteases may be inhibited through use of inhibitors that are derived from the prodomain of ADAM family proteases. In addition, the discovery of the invention provides a mechanism through which TACE activity can be increased or stimulated through disabling the inhibitory activity of a peptide that inhibits TACE protease activity.

I. Inhibitory Agents

The invention provides inhibitory agents that can inhibit the protease activity of TNF-α converting enzyme (TACE). These inhibitory agents can be used to inhibit the protease activity of TNF-α converting enzyme. As such, these inhibitory agents can be used to reduce numerous pathologies associated with TACE activity. These pathologies and diseases include arthritis, sepsis, ulcerative colitis, multiple sclerosis, Crohn's disease, septic shock, graft rejection, cachexia, insulin resistance, post-ischemic reperfusion injury, tumor metastasis, tissue ulceration, abnormal wound healing, periodontal disease, bone disease, proteinuria, aneurysmal aortic disease, degenerative cartilage loss, demyelinating diseases of the nervous system, and HIV infection.

In one aspect, an inhibitory agent can be a peptide. For example, the inhibitory agent can be a peptide having the amino acid sequence: MRQSLLFLTSVVPFVLAPRPPDDPGFGPHQRLEKLDSLLSDYDILSLSNIQQH S (SEQ ID NO:3). An inhibitory agent of the invention can also be a peptide fragment of a peptide having SEQ ID NO:3 that is able to inhibit the protease activity of TNF-α converting enzyme. Such peptide fragments are exemplified by QRLEKLDSLLSDYDILSLS (SEQ ID NO:4), RLEKLDSLLSDYDILSL (SEQ ID NO:5), VLAPRPP (SEQ ID NO:6), RLEKLDSLLSDYDILSLSNIQQHS (SEQ ID NO:7), and PRPPDDPGFGPHQRLEKLDSLLSDYDILSLSNIQQHS (SEQ ID NO:8). According to the invention, such peptide fragments may be ten amino acids or more in length. However, shorter peptide fragments of SEQ ID NO:3 that contain five, six, seven, eight, or nine amino acids are included within the invention if they are able to inhibit the protease activity of TNF-α converting enzyme. The peptides and peptide fragments of the invention may be in glycosylated form, or in unglycosylated form. A peptide or peptide fragment of the invention may be soluble or insoluble in aqueous solution. A peptide or peptide fragment of the invention may be included within a polyprotein that contains multiple peptides or peptide fragments which are continuously connected by amino acid linkers. These linkers may be designed to include sites that are recognized and cleaved through use of processes such as treatment with chemicals or proteases.

An inhibitory agent may be a coupled protein having a partner protein coupled to a peptide or peptide fragment of the invention. A coupled protein of the invention does not include a protein having GenBank accession number Q9Z0F8, Q9Z1K9, P78536, or Q9VAC5. In some aspects, a coupled protein of the invention may include a cysteine switch motif. A cysteine switch motif is exemplified by PKVCGY (SEQ ID NO:2) or PKTCGY (SEQ ID NO:9). In other aspects, a coupled protein of the invention may not include a cysteine switch motif as exemplified above.

The partner protein may be used to increase or decrease the solubility of the coupled protein. The partner protein may also be a carrier protein that is used to increase the immunogenicity of the coupled protein to increase production of antibodies that bind to a peptide of the invention. Numerous carrier proteins may be used to create coupled proteins of the invention. Examples of such carrier proteins include, keyhole limpet hemacyanin, bovine serum albumin, ovalbumin, mouse serum albumin, rabbit serum albumin, and the like.

The partner protein may also be used to provide for the separation or detection of a coupled protein. Accordingly, a coupled protein can be detected or isolated by interaction with other components that bind to the partner protein portion of the coupled protein. For example, a coupled protein having avidin as a partner protein can be detected or separated with biotin through use of known methods.

A partner protein may also be used to cause the coupled protein to form an inclusion body upon expression within a cell. A partner protein can also be an export signal that causes export of a coupled protein, a polyprotein, or peptide out of a cell. In addition, a partner protein can direct a coupled protein, polyprotein, or peptide to a compartment within a cell, such as the periplasm.

A partner protein may be coupled to a polyprotein or a peptide of the invention by creation of a fusion protein through use of recombinant methods. A partner protein may also be coupled to a polyprotein or peptide of the invention through use of chemical linking methods, or through use of a chemical linker. Such coupling methods are known in the art and have been described. Harlow et al., Antibodies: A Laboratory Manual, page 319 (Cold Spring Harbor Pub. 1988); Taylor, *Protein Immobilization*, Marcel Dekker, Inc., New York, (1991).

An inhibitory agent may be a variant of a peptide having an amino acid sequence that is altered relative to SEQ ID NO:3, and peptide fragments thereof, that inhibits the protease activity of TNF-α converting enzyme. A variant of a peptide can be a deletion, addition, or subtraction of one or more amino acids at the amino-terminal and/or carboxyl-terminal end of a peptide of the invention. For example, a variant of a peptide may include one, two, five, ten or twenty amino acids on the amino-terminal, carboxyl-terminal, or both the amino-terminal and carboxyl-terminus of the peptide. In another example, a variant of a peptide may have one, two, five, ten or twenty amino acids deleted from the amino-terminal, carboxyl-terminal, or both the amino-terminal and carboxyl-terminus of the peptide. A variant of a peptide can also be a deletion, addition or subtraction of one or more amino acids at one or more sites within a peptide of the invention. For example, a variant of a peptide may have one, two, five, seven, or ten amino acids inserted or deleted from a site within a peptide of the invention. Methods for such manipulations are generally known in the art. For example, amino acid sequence variants of SEQ ID NO:3 can be prepared by mutagenesis of DNA encoding the peptide. Methods for mutagenesis and nucleotide sequence alterations are well known in the art. See, for example, Kunkel, *Proc. Natl. Acad. Sci. USA*, 82, 488 (1985); Kunkel et al., *Methods in Enzymol.*, 154:367 (1987); U.S. Pat. No. 4,873,192; Walker and Gaastra, eds., *Techniques in Molecular biology*, MacMillan Publishing Company, New York (1983) and the references cited therein. Guidance as to appropriate amino acid substitutions may be found in the model of Dayhoff et al., *Atlas of Protein Sequence and Structure*, Natl. Biomed. Res. Found., Washington, C.D. (1978), herein incorporated by reference.

An inhibitory agent may be a variant of a peptide of the invention that contains one or more amino acid substitutions in the amino acid sequence as put forth in SEQ ID NO:3, and fragments thereof, that inhibit the protease activity of TNF-α converting enzyme. Conservative amino acid substitutions are preferred and include, for example; exchange of aspartic acid and glutamic acid as acidic amino acids; exchange of lysine and arginine or histidine as basic amino acids; exchange of leucine and isoleucine; exchange of methionine and valine, or alanine and valine as hydrophobic amino acids; or exchange of serine and glycine, alanine, or threonine as hydrophilic amino acids. Conservative amino acid substitution also includes groupings based on side chains. Members in each group can be substituted for one another. For example, a group of amino acids having aliphatic side chains is glycine, alanine, valine, leucine, and isoleucine. These may be substituted for one another. A group of amino acids having aliphatic-hydroxyl side chains is serine and threonine. A group of amino acids having amide-containing side chains is asparagine and glutamine. A group of amino acids having aromatic side chains is phenylalanine, tyrosine, and tryptophan. A group of amino acids having basic side chains is lysine, arginine, and histidine. A group of amino acids having sulfur-containing side chains is cysteine and methionine. For example, replacement of a leucine with an isoleucine or valine, an aspartate with a glutamate, a threonine with a serine, or a similar replacement of an amino acid with a structurally related amino acid may be accomplished to produce a variant peptide of the invention.

An inhibitory agent may be a peptidomimetic of a peptide or peptide fragment of the invention. A peptidomimetic describes a peptide analog, such as those commonly used in the pharmaceutical industry as non-peptide drugs, with properties analogous to those of the template peptide. (Fauchere, J., *Adv. Drug Res.*, 15: 29 (1986) and Evans et al., *J. Med. Chem.*, 30:1229 (1987)). Peptidomimetics are structurally similar to peptides having peptide bonds, but have one or more peptide linkages optionally replaced by a linkage such as, —$CH_2NH$—, —$CH_2S$—, —$CH_2$—$CH_2$—, —CH=CH— (cis and trans), —$COCH_2$—, —CH(OH) $CH_2$—, and —$CH_2SO$—, by methods known in the art. Advantages of peptide mimetics over natural peptide embodiments may include more economical production, greater chemical stability, altered specificity and enhanced pharmacological properties such as half-life, absorption, potency and efficacy.

Peptides, peptide fragments, coupled proteins, and peptidomimetics of the invention can be modified for in vivo use by the addition, at the amino-terminus and/or the carboxyl-terminus, of a blocker to decrease degradation in vivo. This can be useful in those situations in which the peptide termini tend to be degraded by proteases in vivo. Such blockers can include, without limitation, additional related or unrelated peptide sequences that can be attached to the amino and/or carboxyl terminal residues of the peptide, coupled protein, and peptidomimetic to be administered. This can be done either chemically during the synthesis of the peptide, peptide fragment, or coupled protein; or by recombinant DNA technology using methods familiar to artisans of average skill. Alternatively, blockers such as pyroglutamic acid, or other molecules known in the art, can be attached to the amino and/or carboxyl terminal residues, or the amino group at the amino terminus or carboxyl group at the carboxyl terminus can be replaced with a different moiety. Accordingly, the invention provides peptides that are amino-terminally and carboxyl-terminally blocked.

Peptides, peptide fragments, polyproteins, and coupled proteins of the invention can be produced on a small or large scale through use of numerous expression systems that include, but are not limited to, cells or microorganisms that are transformed with a recombinant nucleic acid construct that contains a nucleic acid segment of the invention. Examples of recombinant nucleic acid constructs may include bacteriophage DNA, plasmid DNA, cosmid DNA, or viral expression vectors. Examples of cells and microorganisms that may be transformed include bacteria (for example, *E. coli* or *B. subtilis*); yeast (for example, *Saccharomyces* and *Pichia*); insect cell systems (for example, baculovirus); plant cell systems; or mammalian cell systems (for example, COS, CHO, BHK, 293, VERO, HeLa, MDCK, W138, and NIH 3T3 cells). Also useful as host cells are primary or secondary cells obtained directly from a mammal that are transfected with a plasmid vector or infected with a viral vector. Examples of suitable expression vectors include, without limitation, plasmids and viral vectors such as herpes viruses, retroviruses, vaccinia viruses, attenuated vaccinia viruses, canary pox viruses, adenoviruses, adeno-associated viruses, lentiviruses and herpes viruses, among others. Synthetic methods may also be used to produce polypeptides and peptide fragments of the invention. Such methods are known and have been reported. Merrifield, *Science*, 85:2149 (1963).

II. Nucleic Acid Segments, Expression Cassettes, and Nucleic Acid Constructs of the Invention The present invention provides isolated nucleic acid segments that encode the peptides and coupled proteins of the invention. An isolated nucleic acid segment may be ribonucleic acid or deoxyribonucleic acid. An example of a nucleic acid segment of the invention has the nucleotide sequence: ATGAGGCAGTCTCTCCTATTCCTGAC-CAGCGTGGTTCCTTTCGTGCTGGC GCCGCGACCTC-CGGATGACCCGGGCTTCGGCCCCCACCA-GAGACTCGAG AAGCTTGATTCTTTGCTCTCAGACTAC-GATATTCTCTCTTTATCTAATATC CAGCAGCATTCG-TAA (SEQ ID NO:10). The nucleic acid segments of the invention also include nucleic acid segments that encode the same amino acids due to the degeneracy of the genetic code. For example, the amino acid threonine is encoded by ACU, ACC, ACA and ACG. It is intended that the invention includes all variations of a nucleic acid segment that encodes for the same amino acids. Such mutations are known in the art (Watson et al, Molecular Biology of the Gene, Benjamin Cummings 1987). Mutations also include alteration of a nucleic acid segment to encode conservative amino acid changes. Nucleic acid segments of the invention may also be optimized for expression in a specific organism. For example, a nucleic acid segment may be codon optimized for expression in yeast, human, or bacterial cells.

A nucleic acid segment of the invention may be inserted into a vector to create a nucleic acid construct. A vector may include, but is not limited to, any plasmid, phagemid, F-factor, virus, cosmid, or bacteriophage in double or single stranded linear or circular form which may or may not be self transmissible or mobilizable. The vector can also transform a prokaryotic or eukaryotic host either by integration into the cellular genome or exist extrachromosomally (e.g. autonomous replicating plasmid with an origin of replication).

The nucleic acid segment in the vector can be under the control of, and operably linked to, an appropriate promoter or other regulatory elements for transcription in vitro or in a host cell, such as a eukaryotic cell, or a microbe, e.g. bacteria. The vector may be a shuttle vector that functions in multiple hosts. The vector may also be a cloning vector which typically contain one or a small number of restriction endonuclease recognition sites at which foreign DNA sequences can be inserted in a determinable fashion. Such insertion can occur without loss of essential biological function of the cloning vector. A cloning vector may also contain a marker gene that is suitable for use in the identification and selection of cells transformed with the cloning vector. Examples of marker genes are tetracycline resistance or ampicillin resistance. Many cloning vectors are commercially available (Stratagene, New England Biolabs, Clonetech).

The nucleic acid segments of the invention may also be inserted into an expression vector to create a nucleic acid construct. Typically an expression vector contains prokaryotic DNA elements coding for a bacterial replication origin and an antibiotic resistance gene to provide for the amplification and selection of the expression vector in a bacterial host; regulatory elements that control initiation of transcription such as a promoter; and DNA elements that control the processing of transcripts such as introns, or a transcription termination/polyadenylation sequence.

Multiple nucleic acid segments encoding a peptide or coupled protein of the invention may be inserted into a vector, such as an expression vector. These multiple nucleic acid segments can be continuously connected such that a polyprotein containing peptides of the invention connected by linkers is expressed from the expression vector. Such a polyprotein can be isolated and then cleaved to produce peptides or coupled proteins of the invention. The polyprotein can be cleaved through use of numerous methods, such as chemical or protease cleavage. Accordingly, linker sequences can be designed to be cleaved by specific proteases or chemicals. Examples of chemicals that can be used to cleave polyproteins of the invention include cyanogen bromide, Formic acid (70%) and heat, hydroxylamine at pH 9 and heat, iodosobenzoic acid-2-(2-nitrophenyl)-3-methyl-3-bromoindole-nine in 50% acetic acid, and the like. Examples of enzymes that can be used to cleave polyproteins of the invention include Ala-64 subtilisin, clostripain, collagenase, enterokinase, factor Xa, renin, α-thrombin, trypsin, tobacco etch virus protease, and the like.

A polyprotein containing multiple peptides or peptide fragments that are connected by linker sequences, and a partner protein that allows the polyprotein to be isolated can also be expressed. For example, an expression cassette can be designed to express a polyprotein that includes biotin coupled to ten copies of a peptide of the invention that are connected to each other by a chemical or protease cleavable linker. The polyprotein can be expressed within a cell and then bound to an avidin support such that the polyprotein is immobilized. Cellular contaminants can then be washed away to allow isolation of the polyprotein. The polyprotein can then be cleaved to release peptides of the invention. These peptides can be purified through use of numerous art recognized methods, such as gel filtration chromatography, ion exchange chromatography, and the like.

Methods to introduce a nucleic acid segment into a vector are well known in the art (Sambrook et al., Molecular Cloning: A Laboratory Manual, 3rd edition, Cold Spring Harbor Press, Cold Spring Harbor, N.Y. (2001)). Briefly, a vector into which a nucleic acid segment is to be inserted is treated with one or more restriction enzymes (restriction endonuclease) to produce a linearized vector having a blunt end, a "sticky" end with a 5' or a 3' overhang, or any combination of the above. The vector may also be treated with a restriction enzyme and subsequently treated with another modifying enzyme, such as a polymerase, an exonuclease, a phosphatase or a kinase, to create a linearized vector that has characteristics useful for ligation of a polynucleic acid segment into the vector. The nucleic acid segment that is to be inserted into the vector is treated with one or more restriction enzymes to create a linearized segment having a blunt end, a "sticky" end with a 5' or a 3' overhang, or any combination of the above. The nucleic acid segment may also be treated with a restriction enzyme and subsequently treated with another DNA modifying enzyme. Such DNA modifying enzymes include, but are not limited to, polymerase, exonuclease, phosphatase or a kinase, to create a nucleic acid segment that has characteristics useful for ligation of a nucleic acid segment into the vector.

The treated vector and nucleic acid segment are then ligated together to form a construct containing a nucleic acid segment according to methods known in the art (Sambrook et al., Molecular Cloning: A Laboratory Manual, 3rd edition, Cold Spring Harbor Press, Cold Spring Harbor, N.Y. (2001)). Briefly, the treated nucleic acid fragment and the treated vector are combined in the presence of a suitable buffer and ligase. The mixture is then incubated under appropriate conditions to allow the ligase to ligate the nucleic acid fragment into the vector.

The invention also provides an expression cassette which contains a regulatory sequence capable of directing expression of a particular nucleic acid segment of the invention, such as SEQ ID NO:10, either in vitro or in a host cell. The expression cassette is an isolatable unit such that the expression cassette may be in linear form and functional within in vitro transcription and translation assays. The materials and procedures to conduct these assays are commercially available from Promega Corp. (Madison, Wisconsin). For example, an in vitro transcript may be produced by placing a nucleic acid segment under the control of a T7 promoter and then using T7 RNA polymerase to produce an in vitro transcript. This transcript may then be translated in vitro through use of a rabbit reticulocyte lysate. Alternatively, the expression cassette can be incorporated into a vector allowing for replication and amplification of the expression cassette within a host cell or also in vitro transcription and translation of a nucleic acid segment.

Such an expression cassette may contain one or a plurality of restriction sites allowing for placement of the nucleic acid segment under the regulation of a regulatory sequence. The expression cassette can also contain a termination signal operably linked to the nucleic acid segment as well as regulatory sequences required for proper translation of the nucleic acid segment. The expression cassette containing the nucleic acid segment may be chimeric, meaning that at least one of its components is heterologous with respect to at least one of its other components. The expression cassette may also be one which is naturally occurring but has been obtained in a recombinant form useful for heterologous expression. Expression of the nucleic acid segment in the expression cassette may be under the control of a constitutive promoter or an inducible promoter which initiates transcription only when the host cell is exposed to some particular external stimulus.

The expression cassette may include in the 5'-3' direction of transcription, a transcriptional and translational initiation region, a nucleic acid segment and a transcriptional and translational termination region functional in vivo and/or in vitro. The termination region may be native with the transcriptional initiation region, may be native with the nucleic acid segment, or may be derived from another source.

The regulatory sequence can be a polynucleotide sequence located upstream (5' non-coding sequences), within, or downstream (3' non-coding sequences) of a coding sequence, and which influences the transcription, RNA processing or stability, or translation of the associated coding sequence. Regulatory sequences can include, but are not limited to, enhancers, promoters, repressor binding sites, translation leader sequences, introns, and polyadenylation signal sequences. They may include natural and synthetic sequences as well as sequences which may be a combination of synthetic and natural sequences. While regulatory sequences are not limited to promoters, some useful regulatory sequences include constitutive promoters, inducible promoters, regulated promoters, tissue-specific promoters, viral promoters and synthetic promoters.

A promoter is a nucleotide sequence which controls the expression of the coding sequence by providing the recognition for RNA polymerase and other factors required for proper transcription. A promoter includes a minimal promoter, consisting only of all basal elements needed for transcription initiation, such as a TATA-box and/or initiator that is a short DNA sequence comprised of a TATA-box and other sequences that serve to specify the site of transcription initiation, to which regulatory elements are added for control of expression. A promoter may be derived entirely from a native gene, or be composed of different elements derived from different promoters found in nature, or even be comprised of synthetic DNA segments. A promoter may contain DNA sequences that are involved in the binding of protein factors which control the effectiveness of transcription initiation in response to physiological or developmental conditions.

The invention also provides a construct containing a vector and an expression cassette. The vector may be selected from, but not limited to, any vector previously described. Into this vector may be inserted an expression cassette through methods known in the art and previously described (Sambrook et al., Molecular Cloning: A Laboratory Manual, 3rd edition, Cold Spring Harbor Press, Cold Spring Harbor, N.Y. (2001)). In one embodiment, the regulatory sequences of the expression cassette may be derived from a source other than the vector into which the expression cassette is inserted. In another embodiment, a construct containing a vector and an expression cassette is formed upon insertion of a nucleic acid segment of the invention into a vector that itself contains regulatory sequences. Thus, an expression cassette is formed upon insertion of the nucleic acid segment into the vector. Vectors containing regulatory sequences are available commercially and methods for their use are known in the art (Clonetech, Promega, Stratagene).

III. Antibodies and Aptamers

The invention provides antibodies and aptamers that bind to peptides of the invention. For example, an antibody or aptamer of the invention can specifically bind to a peptide having an amino acid sequence corresponding to SEQ ID NO:3. Such antibodies and aptamers are thought to be useful for disabling or reducing the inhibitory activity of a peptide that inhibits TACE protease activity. Accordingly, the antibodies and aptamers of the invention may be used to increase TACE activity. Increasing TACE activity may be used to increase the concentration of mature TNF-α and allow apoptosis to be induced for the elimination of tumor cells.

Antibodies can be prepared using a peptide or a coupled protein as the immunizing antigen. The peptide or coupled protein used to immunize an animal can be derived from translated cDNA or chemical synthesis.

If desired, polyclonal or monoclonal antibodies can be purified, for example, by binding to and elution from a matrix to which the peptide to which the antibodies were raised is bound. Those of skill in the art will know of various techniques common in the immunology arts for purification and/or concentration of polyclonal antibodies, as well as monoclonal antibodies (Coligan, et al., Unit 9, Current Protocols in Immunology, Wiley Interscience, 1991, incorporated by reference).

A suitable antibody is specific for at least one region of the peptide. For example, one of skill in the art can use a peptide to generate appropriate antibodies of the invention. Antibodies of the invention include polyclonal antibodies, monoclonal antibodies, and fragments of polyclonal and monoclonal antibodies.

The preparation of polyclonal antibodies is well-known to those skilled in the art (Green et al., Production of Polyclonal Antisera, in Immunochemical Protocols (Manson, ed.), pages 1-5 (Humana Press 1992); Coligan et al., Production of Polyclonal Antisera in Rabbits, Rats, Mice and Hamsters, in Current Protocols in Immunology, section 2.4.1 (1992), which are hereby incorporated by reference). For example, a peptide or coupled protein is injected into an animal host, preferably according to a predetermined schedule incorporating one or more booster immunizations, and the animal is bled periodically. Polyclonal antibodies specific for the peptide may then be purified from such antisera by, for example, affinity chromatography using the peptide coupled to a suitable solid support.

The preparation of monoclonal antibodies likewise is conventional (Kohler & Milstein, *Nature,* 256:495 (1975); Coligan et al., sections 2.5.1-2.6.7; and Harlow et al., Antibodies: A Laboratory Manual, page 726 (Cold Spring Harbor Pub. 1988)), which are hereby incorporated by reference. Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (Coligan et al., sections 2.7.1-2.7.12 and sections 2.9.1-2.9.3; Barnes et al., Purification of Immunoglobulin G (IgG), in Methods in Molecular Biology, Vol. 10, pages 79-104 (Humana Press 1992)). Methods of in vitro and in vivo multiplication of monoclonal antibodies is well-known to those skilled in the art. Multiplication in vitro may be carried out in suitable culture media such as Dulbecco's Modified Eagle Medium or RPMI 1640 medium, optionally replenished by a mammalian serum such as fetal calf serum or trace elements and growth-sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an air reactor, in a continuous stirrer reactor, or immobilized or entrapped cell culture. Multiplication in vivo may be carried out by injecting cell clones into mammals histocompatible with the parent cells, e.g., osyngeneic mice, to cause growth of antibody-producing tumors. Optionally, the animals are primed with a hydrocarbon, especially oils such as pristine tetramethylpentadecane prior to injection. After one to three weeks, the desired monoclonal antibody is recovered from the body fluid of the animal.

Antibodies can also be prepared through use of phage display techniques. In one example, an organism is immunized with an antigen, such as a peptide or coupled protein of the invention. Lymphocytes are isolated from the spleen of the immunized organism. Total RNA is isolated from the splenocytes and mRNA contained within the total RNA is reverse transcribed into complementary deoxyribonucleic acid (cDNA). The cDNA encoding the variable regions of the light and heavy chains of the immunoglobulin is amplified by polymerase chain reaction (PCR). To generate a single chain fragment variable (scFV) antibody, the light and heavy chain amplification products may be linked by splice overlap extension PCR to generate a complete sequence and ligated into a suitable vector. $E.$ $coli$ are then transformed with the vector encoding the scFV, and are infected with helper phage, to produce phage particles that display the antibody on their surface. Alternatively, to generate a complete antigen binding fragment (Fab), the heavy chain amplification product can be fused with a nucleic acid sequence encoding a phage coat protein, and the light chain amplification product can be cloned into a suitable vector. $E.$ $coli$ expressing the heavy chain fused to a phage coat protein are transformed with the vector encoding the light chain amplification product. The disulphide linkage between the light and heavy chains are established in the periplasm of $E.$ $coli$. The result of this procedure is to produce an antibody library with up to $10^9$ clones. The size of the library can be increased to $10^{18}$ phages by later addition of the immune responses of additional immunized organisms that may be from the same or different hosts. Antibodies that recognize a specific antigen can be selected through panning. Briefly, an entire antibody library can be exposed to an immobilized antigen against which antibodies are desired. Phage that do not express an antibody that binds to the antigen are washed away. Phage that express the desired antibodies are immobilized on the antigen. These phage are then eluted and again amplified in $E.$ $coli$. This process can be repeated to enrich the population of phage that express antibodies that specifically bind to the antigen. After phage are isolated that express an antibody that binds to an antigen, a vector containing the coding sequences for the antibody can be isolated from the phage particles and the coding sequences can be recloned into a suitable vector to produce an antibody in soluble form. Phage display methods to isolate antigens and antibodies are known in the art and have been described (Gram et al., *Proc. Natl. Acad. Sci.*, 89:3576 (1992); Kay et al., Phage display of peptides and proteins: A laboratory manual. San Diego: Academic Press (1996); Kermani et al., *Hybrid*, 14:323 (1995); Schmitz et al., *Placenta*, 21 Suppl. A:S106 (2000); Sanna et al., *Proc. Natl. Acad. Sci.*, 92:6439 (1995)).

An antibody of the invention may be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described (Orlandi et al., *Proc. Nat'l Acad. Sci. USA*, 86:3833 (1989) which is hereby incorporated in its entirety by reference). Techniques for producing humanized monoclonal antibodies are described (Jones et al., *Nature*, 321:522 (1986); Riechmann et al., *Nature*, 332:323 (1988); Verhoeyen et al, *Science*, 239:1534 (1988); Carter et al., *Proc. Nat'l Acad. Sci. USA*, 89:4285 (1992); Sandhu, *Crit. Rev. Biotech.*, 12:437 (1992); and Singer et al., *J. Immunol.*, 150:2844 (1993), which are hereby incorporated by reference).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described (Green et al., *Nature Genet.*, 7:13 (1994); Lonberg et al., *Nature*, 368:856 (1994); and Taylor et al., *Int. Immunol.*, 6:579 (1994), which are hereby incorporated by reference).

Antibody fragments of the invention can be prepared by proteolytic hydrolysis of the antibody or by expression in $E.$ $coli$ of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described (U.S. Pat. Nos. 4,036,945; 4,331,647; and 6,342,221, and references contained therein; Porter, *Biochem. J.*, 73:119 (1959); Edelman et al., Methods in Enzymology, Vol. 1, page 422 (Academic Press 1967); and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise, an association of $V_H$ and $V_L$ chains. This association may be noncovalent (Inbar et al., *Proc. Nat'l Acad. Sci. USA*, 69:2659 (1972)). Alternatively, the variable chains can be linked by an intermolecular disulfide bond or cross-linked by chemicals such as glutaraldehyde (Sandhu, *Crit. Rev. Biotech.*, 12:437 (1992)). Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described (Whitlow et al., Methods: A Companion to Methods in Enzymology, Vol. 2, page 97 (1991); Bird et al., *Science*, 242:423 (1988), Ladner et al., U.S. Pat. No. 4,946, 778; Pack et al., *Bio/Technology*, 11:1271 (1993); and Sandhu, *Crit. Rev. Biotech.*, 12:437 (1992)).

Another form of an antibody fragment is a peptide that forms a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (Larrick et al., Methods: A Companion to Methods in Enzymology, Vol. 2, page 106 (1991)).

The invention also provides aptamers that bind to the peptides of the invention. Aptamers are peptides that bind to a peptide of the invention with affinities that are often comparable to those for monoclonal antibody-antigen complexes. In one example, aptamers can be isolated according to mRNA display through use of a DNA library that contains a promoter, a start codon, a nucleic acid sequence coding for random peptides, and a nucleic acid sequence that codes for a histidine tag. This library is transcribed using a suitable polymerase, such as T7 RNA polymerase, after which a puromycin-containing poly A sequence is ligated onto the 3' end of the newly formed mRNAs. When these mRNAs are translated in vitro, the nascent peptides form covalent bonds to the puromycin of the poly A sequence to form an mRNA-peptide fusion molecule. The mRNA-peptide fusion molecules are then purified through use of Ni-NTA agarose and oligo-dT-cellulose. The mRNA portion of the fusion molecule is then reverse transcribed. The double-stranded DNA/RNA-peptide fusion molecules are then incubated with a peptide of the invention and unbound fusion molecules are washed away. The bound fusion molecules are eluted from the immobilized peptides and are then amplified by PCR. This process may be repeated to select for aptamers having high affinity for the peptides of the invention. The sequence of the nucleic acid coding for the aptamers can then be determined and cloned into a suitable vector. Methods for the preparation of peptide aptamers have been described (Wilson et al., *Proc. Natl. Acad. Sci.*, 98:3750 (2001)). Accordingly, the invention provides aptamers that recognize peptides of the invention.

IV. Pharmaceutical Compositions of the Invention

The invention provides pharmaceutical compositions that can be used to inhibit or stimulate the protease activity of TACE. In one example, a pharmaceutical composition can contain a peptide or coupled protein of the invention, and a pharmaceutically acceptable carrier. In another example, a pharmaceutical composition can contain an antibody or aptamer of the invention, and a pharmaceutically acceptable carrier.

The pharmaceutical compositions of the invention may be prepared in many forms that include tablets, hard or soft gelatin capsules, aqueous solutions, suspensions, and liposomes and other slow-release formulations, such as shaped polymeric gels. An oral dosage form may be formulated such that the peptide, coupled protein, antibody, or aptamer is released into the intestine after passing through the stomach. Such formulations are described in U.S. Pat. No. 6,306,434 and in the references contained therein.

Oral liquid pharmaceutical compositions may be in the form of, for example, aqueous or oily suspensions, solutions, emulsions, syrups or elixirs, or may be presented as a dry product for constitution with water or other suitable vehicle before use. Such liquid pharmaceutical compositions may contain conventional additives such as suspending agents, emulsifying agents, non-aqueous vehicles (which may include edible oils), or preservatives.

A peptide, peptide fragment, coupled protein, antibody, or aptamer can be formulated for parenteral administration (e.g., by injection, for example, bolus injection or continuous infusion) and may be presented in unit dosage form in ampoules, pre-filled syringes, small volume infusion containers or multi-dose containers with an added preservative. The pharmaceutical compositions may take such forms as suspensions, solutions, or emulsions in oily or aqueous vehicles, and may contain formulatory agents such as suspending, stabilizing and/or dispersing agents.

Pharmaceutical compositions suitable for rectal administration can be prepared as unit dose suppositories. Suitable carriers include saline solution and other materials commonly used in the art.

For administration by inhalation, a peptide, peptide fragment, coupled protein, antibody or aptamer can be conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, a peptide, peptide fragment, coupled protein, antibody, or aptamer may take the form of a dry powder composition, for example, a powder mix of a modulator and a suitable powder base such as lactose or starch. The powder composition may be presented in unit dosage form in, for example, capsules or cartridges or, e.g., gelatin or blister packs from which the powder may be administered with the aid of an inhalator or insufflator. For intra-nasal administration, a peptide, antibody, or aptamer may be administered via a liquid spray, such as via a plastic bottle atomizer.

Pharmaceutical compositions of the invention may also contain other ingredients such as flavorings, colorings, antimicrobial agents, preservatives, or known TACE inhibitors (Moss et al., *Drug Discovery Today*, 6:417 (2001)).

It will be appreciated that the amount of a peptide, peptide fragment, coupled protein, antibody, or aptamer required for use in treatment will vary not only with the particular carrier selected but also with the route of administration, the nature of the condition being treated and the age and condition of the patient. Ultimately the attendant health care provider may determine proper dosage. In addition, a pharmaceutical composition may be formulated as a single unit dosage form.

V. Methods to Inhibit or Stimulate TACE Activity

The invention provides agents, compositions, and methods to activate or inhibit TACE activity. These methods can be used to increase or decrease the level of tumor necrosis factor alpha in a mammal. In one aspect, the methods involve contacting a cell with an agent of the invention that inhibits the activity of TACE. For example, the cell may be contacted with a peptide of the invention to inhibit the activity of TACE. In other aspects, the methods involve contacting a cell with an agent of the invention that causes an increase in TACE activity. For example, a cell may be contacted with an antibody that binds to N-TACE which disallows N-TACE from inhibiting the activity of TACE and thereby causes an increase in TACE activity relative to the TACE activity of the cell prior to being contacted with the antibody. Alternatively, the cell may be contacted with an aptamer that binds to N-TACE to increase TACE activity through a similar mechanism. The methods of the invention can be utilized with numerous mammals. Examples of such mammals include, cats, dogs, sheep, pigs, goats, cattle, horses, humans, and the like. Numerous pathological states and diseases may be reduced or ameliorated through use of the methods of the invention. Examples of such pathologies are provided below.

Inflammation: Tumor necrosis factor alpha (TNF-α) is associated with many inflammatory responses and diseases. Examples of such diseases include lipopolysaccharide-induced septic shock, arthritis, pleurisy, psoriasis, inflammatory bowel disease, sarcoidosis, pulmonary fibrosis, rheumatoid arthritis, and acute respiratory distress disorder.

TNF-α is synthesized as a pro, membrane-anchored form facing the luminal/extracellular side of the secretory pathway. The proTNF-α is release from cells after endoproteolytic cleavage that is mediated by tumor necrosis factor alpha converting enzyme (TACE).

Upon release, TNF-α mediates the recruitment and activation of inflammatory cells to injured or infected tissues (Old, *Science* 230:630 (1985)). Elevated levels of circulating TNF-α have been demonstrated in several acute and chronic pathological states, such as lipopolysaccharide-induced septic shock, arthritis, pleurisy, Crohn's disease, and inflammatory bowel disease (Beutler and Cerami, *Annu. Rev. Biochem.* 57:505 (1988)).

TNF-α antagonists have been used to treat many inflammatory diseases. For example, rheumatoid arthritis has been treated with etanercept, which is a TNF receptor fusion protein that binds TNF-α and effectively diverts endogenous TNF-α away from the TNF receptor on target cells. Etanercept (U.S. Pat. No: 5,605,690) has also been used in combination with methotrexate for the treatment of rheumatoid arthritis. Rheumatoid arthritis has also been treated with infliximab (WO 92/16553) which is a monoclonal antibody targeted against TNF-α. Infliximab has also been used in combination with methotrexate to treat rheumatoid arthritis. Septic shock has also been treated with therapeutics that inhibit release of TNF-α. In another example, Crohn's disease has been treated by inhibiting TNF-α with infliximab.

Accordingly, agents of the invention can be used to inhibit TNF-α production and thereby reduce inflammation.

Growth hormone related pathologies: High affinity growth hormone binding proteins (GHBP) are soluble, circulating forms of the GH receptor extracellular domain. The GH receptor (GHR) is a member of the large family of cytokine receptors characterized by a single transmembrane domain, an extracellular domain responsible for ligand binding, and an intracellular domain involved in signaling through a variety of phosphorylation cascades. GHBP is evolutionarily well conserved in vertebrates. It is found in the blood of all species examined to date, such as teleosts, reptiles, birds, and mammals.

Generation of GHBP occurs via two mechanisms. One mechanism is shedding, which occurs through proteolysis of the full length GHR to form soluble GHBP. The other mechanism is through alternative splicing of the GHR pre-mRNA. Shedding is thought to operate in most species and is the dominant, if not exclusive, mechanism in rabbits, cows, pigs, and humans. The protease responsible for GHR cleavage and GHBP shedding is thought to be TACE (Baumann, *J. Ped. End. Met.*, 14:355 (2001); Baumann and Frank, *J. Endocrin.*, 174:361 (2002)). A number of factors increase GHBP levels. These include, over-nutrition, estrogens, obesity, pregnancy, glucocorticoids, thyroid hormone, insulin, growth hormone, and GnRH (humans). Factors that decrease GHBP levels include aging, uncontrolled diabetes, catabolic states, renal failure, hypothyroidism, malnutrition, estrogens (rabbits), androgens, IGF-I (humans), Laron syndrome, and GnRH (rats).

Accordingly, the agents and compositions of the invention may be used to increase or decrease the production of GHBP by either stimulating or inhibiting the action of TACE. For example, N-TACE may be administered alone or in combination with other therapeutics to a vertebrate, such as a mammal, to inhibit TACE activity and thereby reduce the production of GHBP and lower the concentration of GHBP in the circulatory system of the vertebrate. Alternatively, an antibody or aptamer may be administered to a vertebrate to increase TACE activity and thereby increase production of GHBP and increase the concentration of GHBP in the circulatory system of the vertebrate.

Cell proliferation and metastasis: The agents and compositions of the invention can be used to induce apoptosis of a target cell by increasing levels of tumor necrosis factor alpha. Accordingly, the methods of the invention can be used to reduce or eliminate growth of tumors by inducing apoptosis of target cancer cells.

The agents and compositions of the invention can also be used to reduce or eliminate proliferation, migration, invasion, and metastasis of cells through epidermal growth factor receptor (EGFR) mediated autocrine signaling.

Ligands that activate the epidermal growth factor receptor are synthesized as membrane-anchored precursors that are proteolytically released by specific metalloproteinases. A variety of ligands have been shown to stimulate the epidermal growth factor receptor. These ligands include epidermal growth factor, transforming growth factor alpha (TGF-α), amphiregulin (AR); heparin-binding epidermal growth factor, and betacellulin. All of these ligands are made as membrane-spanning prohormones that are processed and released through regulated proteolysis (Massague and Pandiella, *Annu. Rev. Biochem.*, 62:515 (1993)).

Matrix metalloproteinases have been shown to participate in the growth and spread of metastatic tumors through release of EGFR ligands (Dong et al., *Proc. Natl. Acad. Sci. USA*, 96:6235 (1999); Wang et al., *Cancer Res.*, 54:4726 (1994); Parsons et al., *Eur. J. Surg. Oncol.*, 23:526 (1997)). It has been shown that metalloprotease inhibitors decrease cell proliferation in direct proportion to their effect on transforming growth factor alpha release. Metalloprotease inhibitors also reduced growth of EGF-responsive tumorigenic cell lines. Blocking release of EGFR ligands strongly inhibits autocrine activation of the epidermal growth factor receptor and reduces both the rate and persistence of cell migration (Dong et al., *Proc. Natl. Acad. Sci. USA*, 96:6235 (1999)). Thus, compounds that inhibit the action of matrix metalloproteinases, such as batimastat, can be used to treat malignant disease by decreasing the invasion, proliferation, migration, and metastasis of tumor cells.

TACE has been show to participate in TGF-α processing (Peschon et al., *Science*, 282:1281 (1988)). Thus, the activity of TACE can be inhibited to decrease or eliminate the release of TGF-α. Inhibition of TGF-α release will then reduce or eliminate TGF-α mediated growth, proliferation, or metastasis of cells.

Accordingly, the agents and compositions of the invention can be used to inhibit TACE activity to reduce or eliminate TGF-α mediated growth, proliferation, or metastasis of cells, such as tumor cells. In addition, the agents of the invention can be formulated in combination with other anti-cancer therapeutics. For example, the agents of the invention can be formulated in combination with anti-neoplastic agents (Merck Index, Merck & Co., Whitehouse Station, N.J.).

Alzheimer's disease: The invention provides agents, compositions, and methods that may be used to reduce amyloid plaque formation in brain tissue.

The amyloid protein, Aβ, which accumulates in the brains of Alzheimer's patients is derived by proteolysis of the amyloid protein precursor (APP) (Younkin, *Ann. Neurol.*, 37:287 (1995); Selkoe, *J. Biol. Chem.*, 271:18295 (1996); Hardy, *Proc. Natl. Acad. Sci. USA*, 94:2095 (1997)). APP can undergo endoproteolytic processing at three sites, one at the amino terminus of the Aβ domain (β-cleavage), one within the Aβ domain (α-cleavage), and one at the carboxyl terminus of the Aβ domain (γ-cleavage). It has been shown that stimulation of APP α-cleavage leads to a significant decrease in Aβ formation. It has also been shown that activation of protein kinase C and/or inhibition of protein phosphatase 1 leads to increased formation and secretion of soluble APP together with a decrease in the formation and secretion of Aβ (Buxbaum et al., *Proc. Natl. Acad. Sci. USA*, 90:9195 (1993); Gabuzda et al., *J. Neurochem.*, 61:2326 (1993); Hung et al., *J. Biol. Chem.*, 268:22959 (1993)).

TACE has been shown to be primarily responsible for the regulated secretion of APP (Buxbaum et al., *J. Biol. Chem.*, 273:27765 (1998)). Accordingly, stimulation of TACE activity may be used to increase the proteolytic processing of APP and decrease Aβ formation.

The invention provides agents that may be used to increase TACE activity. These agents include antibodies and aptamers that bind N-TACE and disallow N-TACE from inhibiting the action of TACE. The agents of the invention may also be combined with other activators of TACE activity, such as 4-aminophenylmercuric acetate (APMA), organomercurials, oxidants, and detergents (Galazka et al., *Biochemistry*, 35:11221 (1996); Milla et al., *J. Biol. Chem.*, 274:30563 (1999)). These agents may also be formulated into pharmaceutical compositions.

EXAMPLES

Example I

Identification and Cloning of N-TACE cDNA

The NCI-H292 cell line was purchased from ATCC (Manassas, Va.) and was grown in RPMI-1640 supplemented with 5% fetal bovine serum (Biofluids, Rockville, Md.). Total RNA was isolated utilizing the RNeasy Maxi Kit (Qiagen Inc., Valencia, Calif.). RT-PCR was performed on total RNA from the NCI-H292 cells utilizing the following primers which amplify the full-length TACE coding region (Genbank Accession Number NM_003183): 5'-CGG-GAA-CAT-GAG-GCA-GTC-TCT-3' (nucleotides 158-178)(SEQ ID NO:11) and 5'-GCA-CTC-TGT-TTC-TTT-GCT-GTT-3' (nucleotides 2616-2636)(SEQ ID NO:12). cDNA products were analyzed by agarose gel electrophoresis and detected by SYBR Green staining (Molecular Probes, Eugene, Oreg.). N-TACE cDNA was cloned into the pcDNA3.1/V5-His-Topo plasmid (Invitrogen, Carlsbad, Calif.) and subjected to double-stranded automated fluorescent sequencing.

Figure 1B:
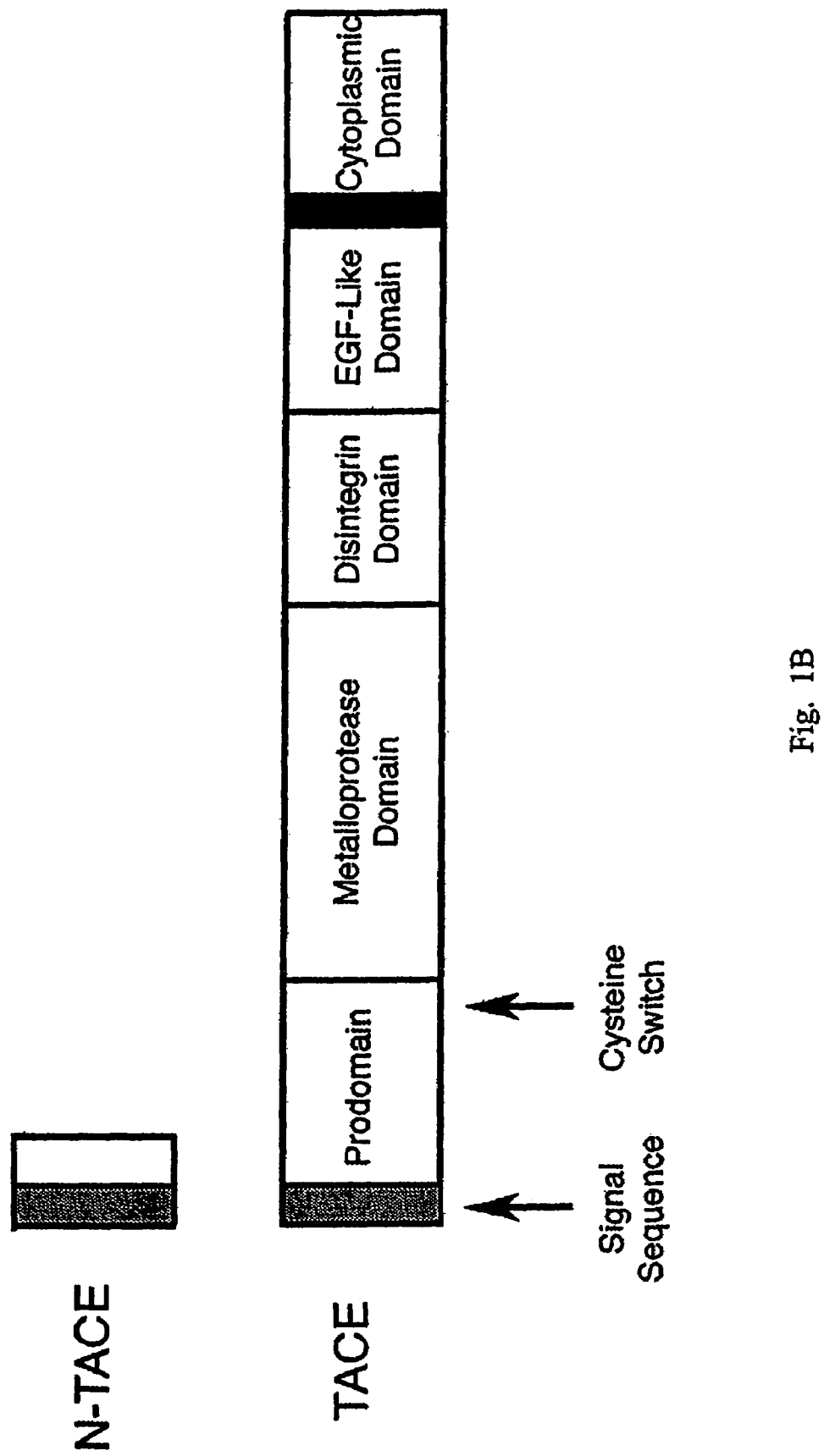
FIG. 1B illustrates the N-TACE protein structure in comparison with the TACE protein structure. N-TACE includes the TACE signal peptide and part of the TACE prodomain. The position of the signal sequence and the cysteine switch are indicated by arrows.
Figure 1C:
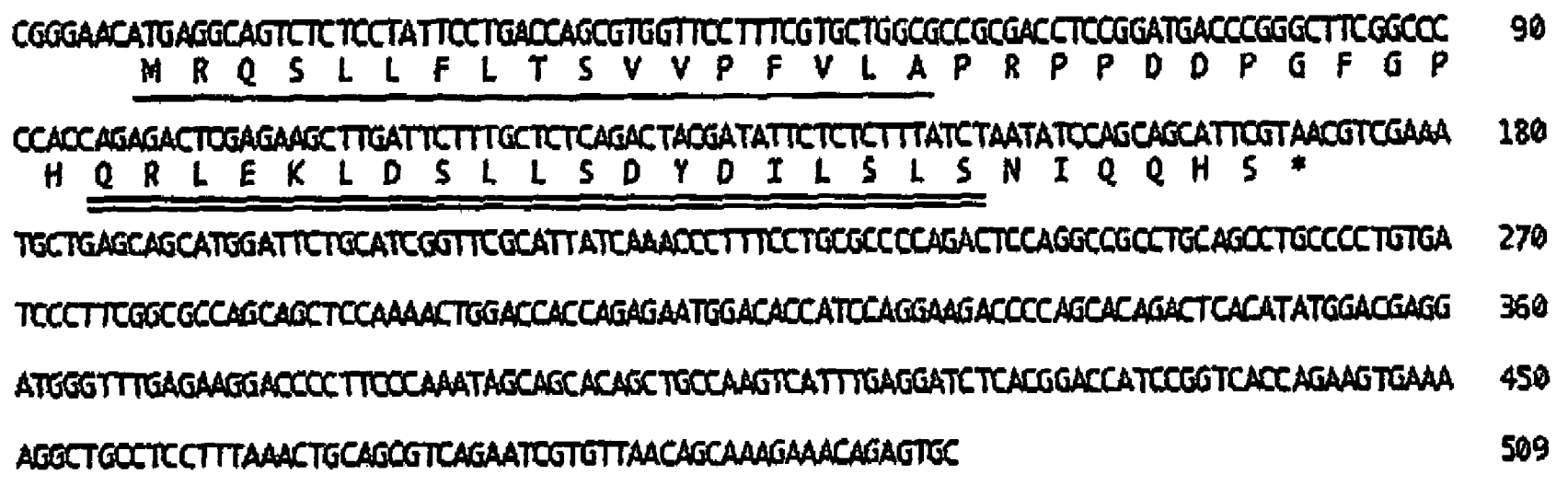
Figure 2A:
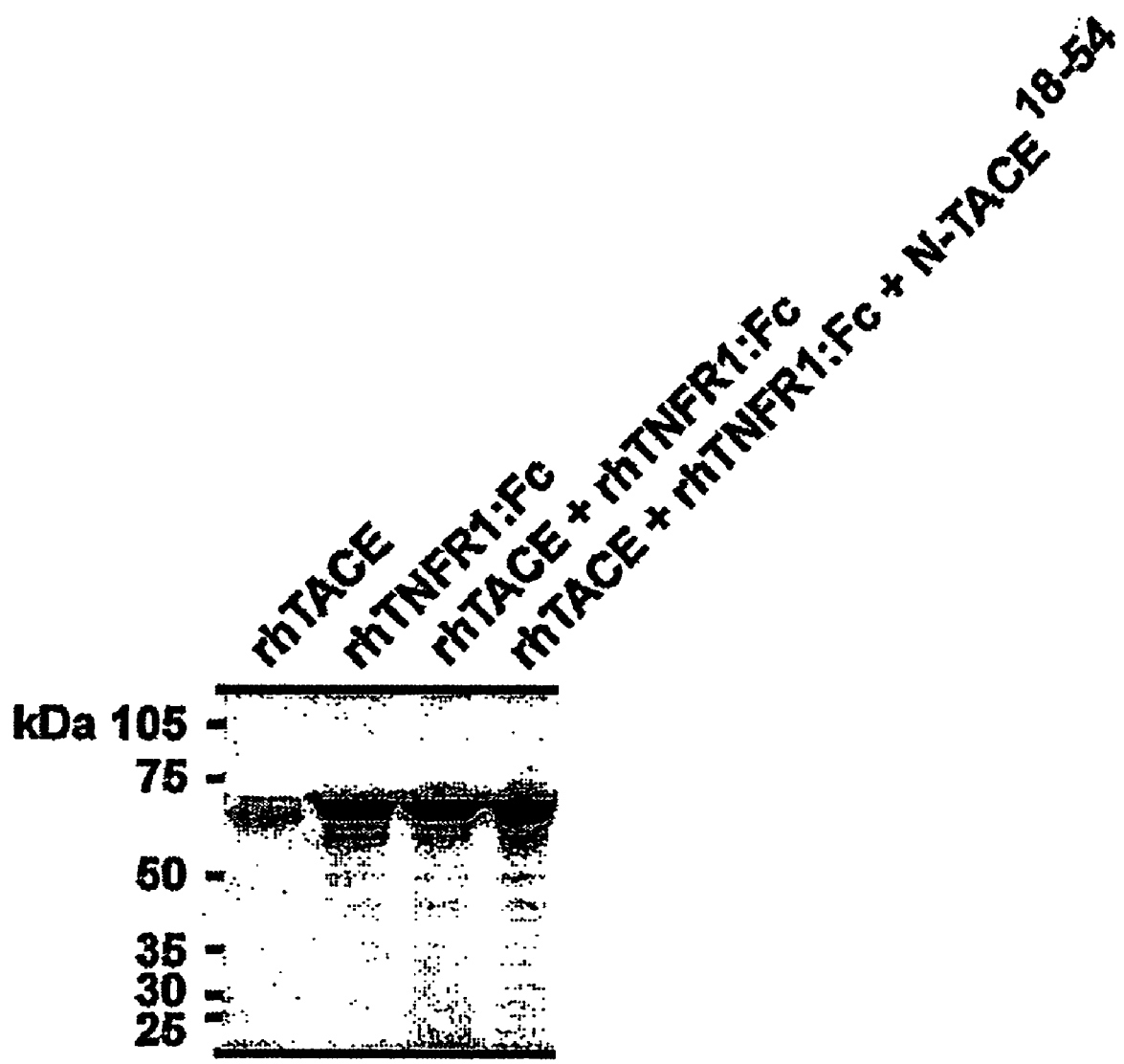
FIGS. 2A-2D illustrate that recombinant human TACE (rhTACE) mediates cleavage of a recombinant human 75-kDa Type II TNF receptor (rhTNFR2), but not a recombinant human 55-kDa Type I TNF receptor (rhTNFR1).
Figure 2B:
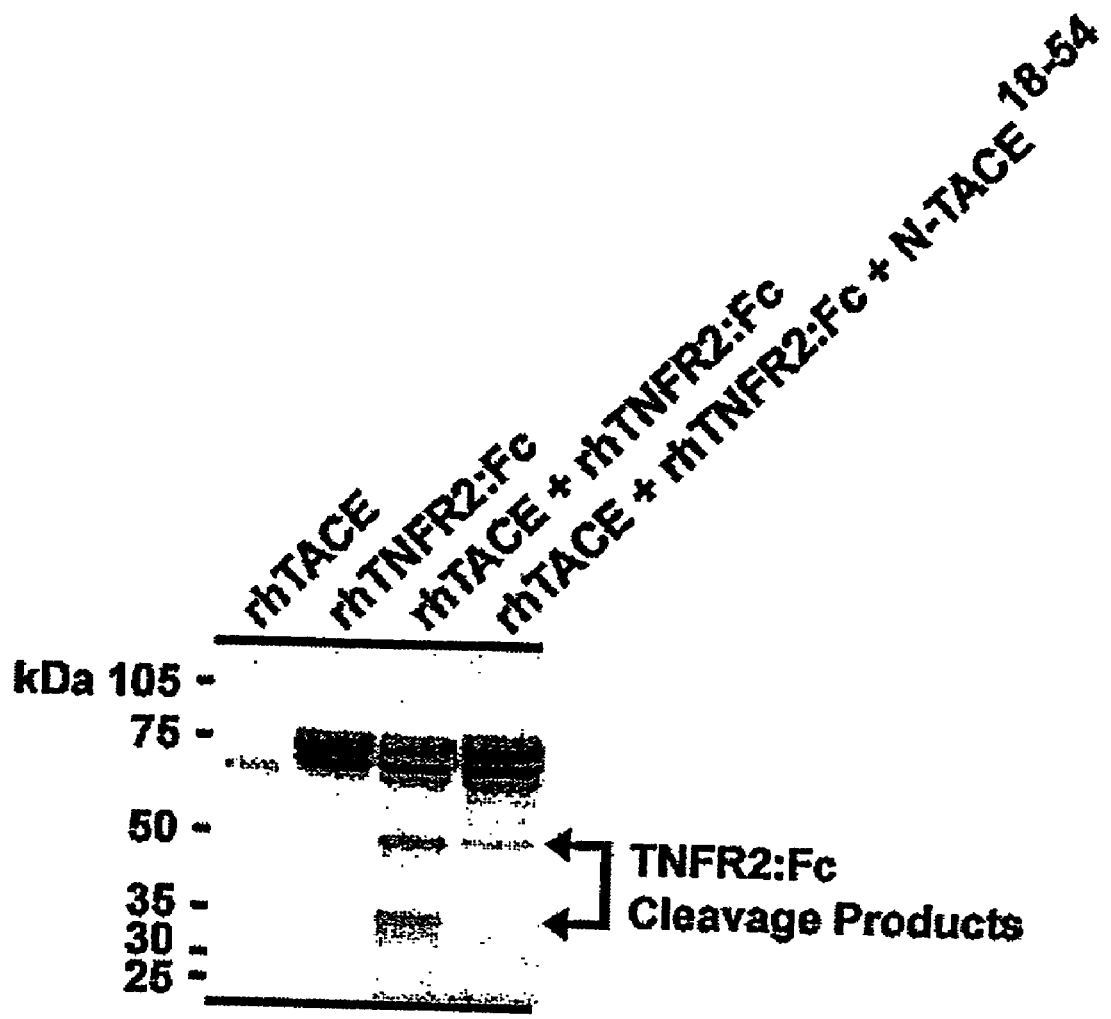
Figure 2C:
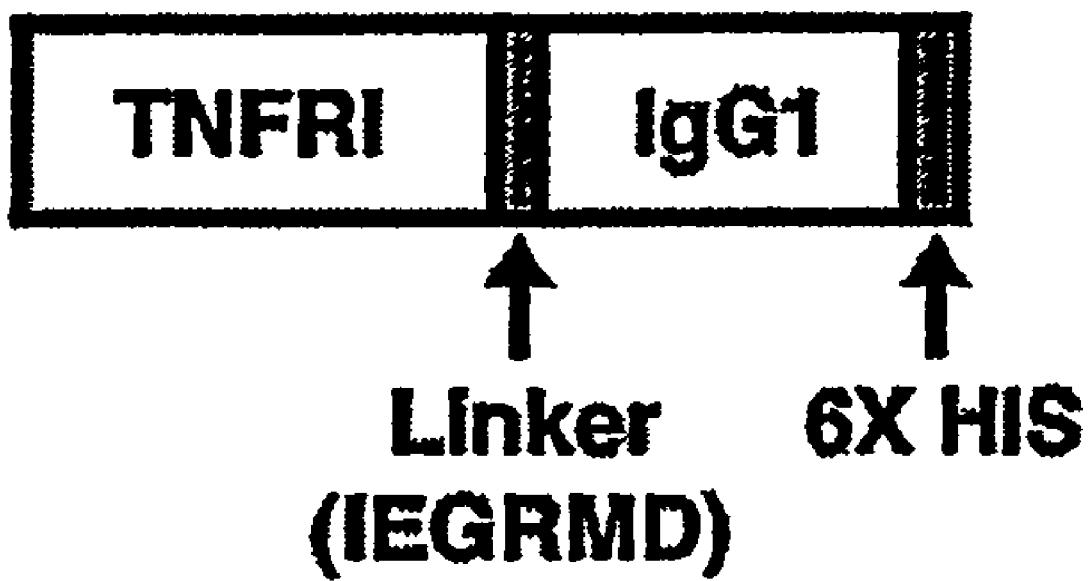
Figure 2D:
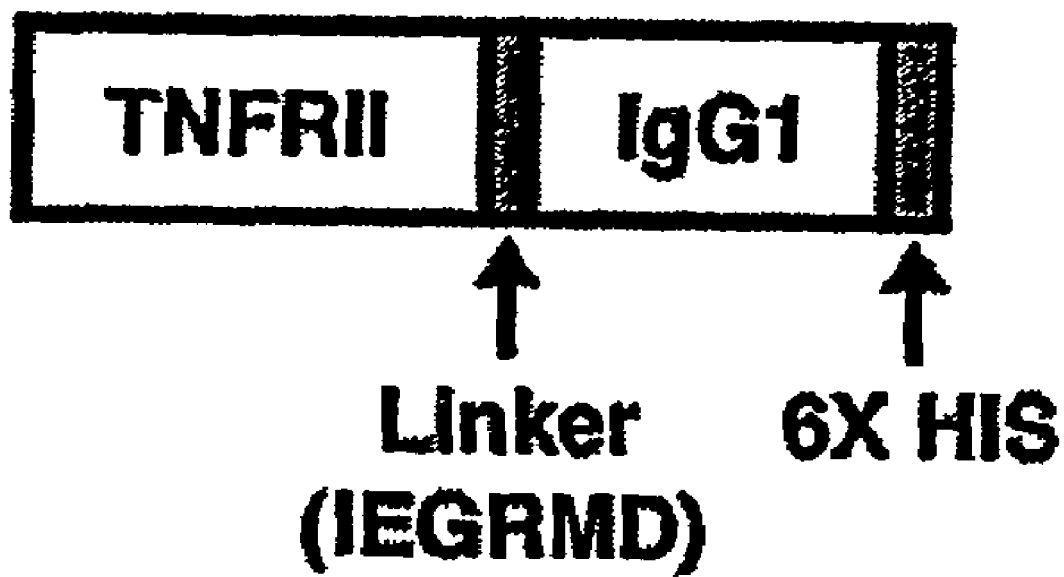

Surprisingly, in addition to the expected 2480-bp full-length TACE cDNA, a 509 bp cDNA was identified which was cloned and sequenced (FIG. 1A). Sequence analysis revealed an open reading frame that encoded the first 54 amino acids of TACE, including the entire signal peptide and the amino-terminus of the prodomain, but not the cysteine switch, the proprotein-convertase cleavage site, or the metalloprotease domain (FIG. 1B). The protein predicted by this open reading frame has a molecular weight of 6.089-kDa and a predicted pI of 5.24. This protein was named N-TACE based upon its homology with the amino-terminus of the full-length TACE protein (FIG. 1C).

Example II

Characterization of N-TACE Inhibitory Activity

A model assay system was developed to assess the ability of N-TACE to inhibit TACE enzymatic activity. Recombinant human TACE (rhTACE), as well as the recombinant human TNFR1:Fc (rhTNFR1:Fc) and TNFR2:Fc (rhTNFR2:Fc) fusion proteins were purchased from R & D Systems (Minneapolis, Minn.). Both TNFR1:Fc and TNFR2:Fc are recombinant human chimeric proteins that encode the extracellular receptor domains, fused to a carboxy-terminal 6X-histidine-tagged Fc region of human IgG1 via a linker peptide (IEGRMD)(SEQ ID NO:1). Recombinant human TACE corresponds to the mature form following removal of the pro-domain and has an apparent molecular weight of 70 kDa. N-TACE(18-54), which lacked the signal peptide, was synthesized by Sigma-Genosys (The Woodlands, Tex.). N-TACE truncation mutants were also synthesized; an amino-terminal mutant N-TACE(18-29) corresponded to N-TACE amino acids 18-29, a mid-domain mutant N-TACE(30-42) corresponded to N-TACE amino acids 30-42, a carboxy-terminal mutant N-TACE(43-54) corresponded to amino acids 43-54, and an extended mid-domain mutant N-TACE(30-48) corresponded to amino acids 30 to 48.

Chou Fasman analysis was performed using MacVector (Accelrys, Burlington, Mass.). Assays (50 µl) were performed in 50 mM Tris, 25 mM NaCl, pH 8.0 at 30° C. for 30 min. Samples were analyzed by SDS-PAGE using 4%-12% Bis-Tris Nupage gels (Invitrogen, Carlsbad, Calif.) and visualized with the SilverQuest Silver Staining Kit (Invitrogen, Carlsbad, Calif.). For Western blot analysis, samples were separated via SDS-PAGE, electroblotted onto nitrocellulose membranes, and incubated overnight (4° C.) with 200 ng/ml of a murine IgG1 monoclonal antibody directed against the histidine tag (Tetra-His, Qiagen, Valenica, Calif.). The antibody detected the carboxy-terminus of the recombinant human TNFR2:Fc fusion protein. A rabbit polyclonal antibody was also generated against N-TACE(18-54) (Sigma-Genosys, The Woodlands, Tex.) and was utilized for Western blotting at a 1:1000 dilution. Detection was by chemiluminescence using horseradish peroxidase-conjugated secondary antibodies.

As shown in FIG. 2, rhTACE cleaved the rhTNFR2:Fc model substrate and generated two predominant cleavage products that were detected by silver staining and Western blotting. Further, the TACE-mediated cleavage of the TNFR2:Fc model substrate was inhibited by 80 μM N-TACE (18-54). In contrast, rhTACE did not cleave the rhTNFR1:Fc model substrate. Therefore, the ability of N-TACE to inhibit TACE activity was assessed utilizing rhTNFR2:Fc as a model target substrate.

Figure 3A:
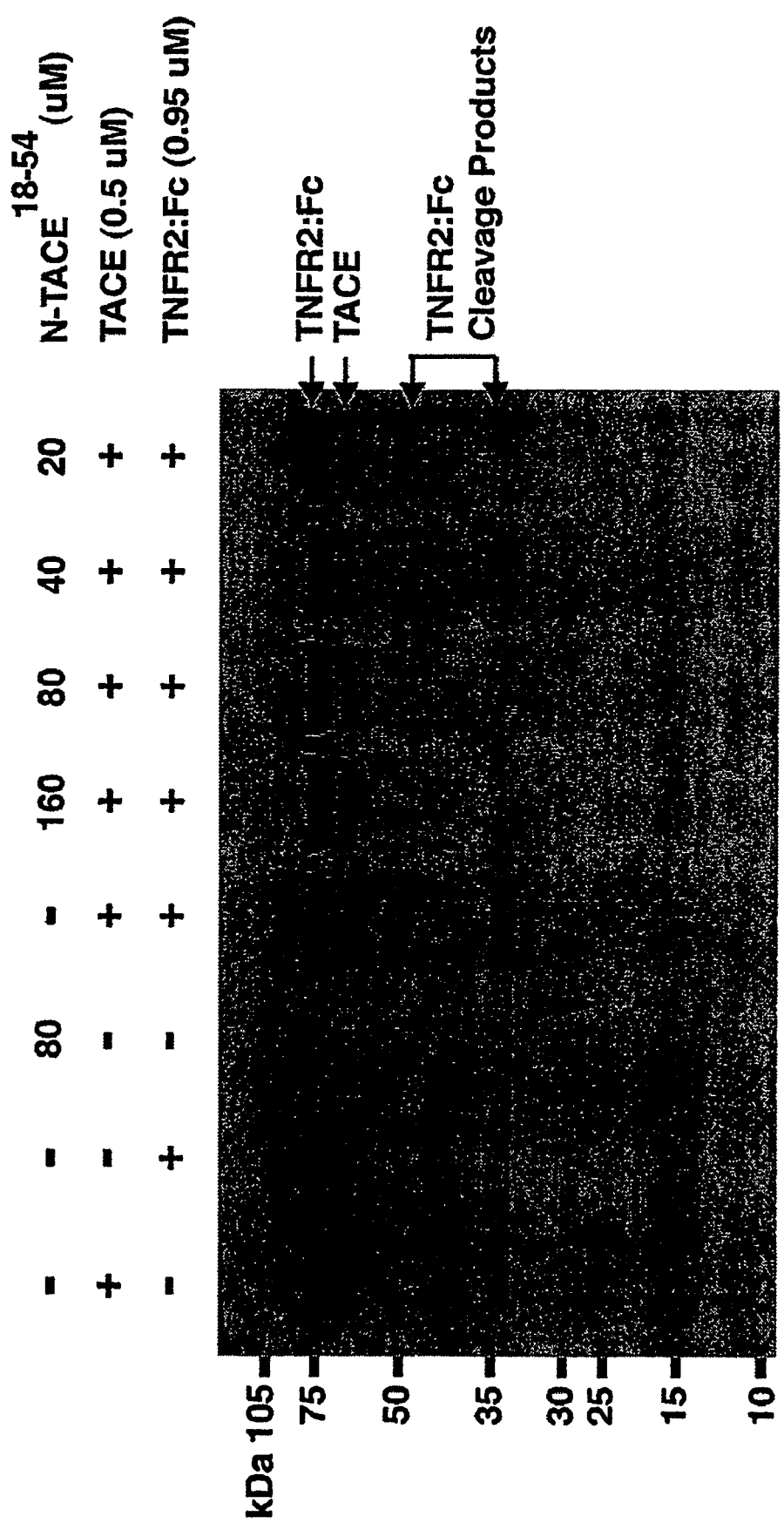
FIGS. 3a-3B show that N-TACE inhibits TNFR2 cleavage by TACE. rhTACE (0.5 µM) was incubated with TNFR2:Fc (0.95 µM) alone, or with concentrations of N-TACE(18-54), ranging from 20 µM to 160 µM, for 30 min.
Figure 3B:
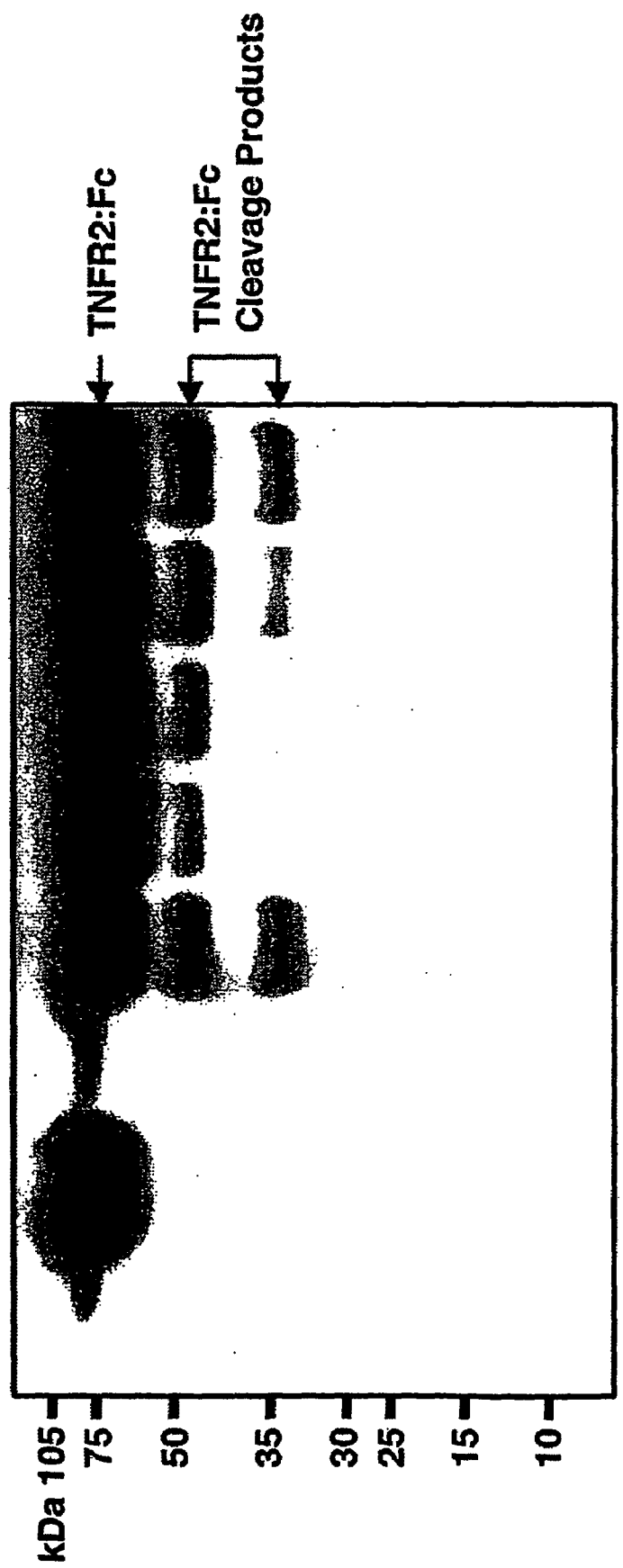

The ability of N-TACE to inhibit TACE enzymatic activity was further assessed. As shown by SDS-PAGE and silver staining in FIG. 3A, the N-TACE(18-54) protein significantly inhibited the proteolytic cleavage of 0.95 μM rhTNFR2:Fc by 0.5 μM rhTACE in a dose-responsive fashion (range: 20 μM to 160 μM) during a 30 min incubation. The identity of TNFR2:Fc and its cleavage products were confirmed by immunoblots utilizing an anti-HIS antibody, which recognizes the carboxy-terminus of the TNFR2:Fc chimeric protein (FIG. 3B). These results demonstrate that N-TACE can function as an inhibitor of TACE proteolytic activity toward TNFR2.

Figure 4:
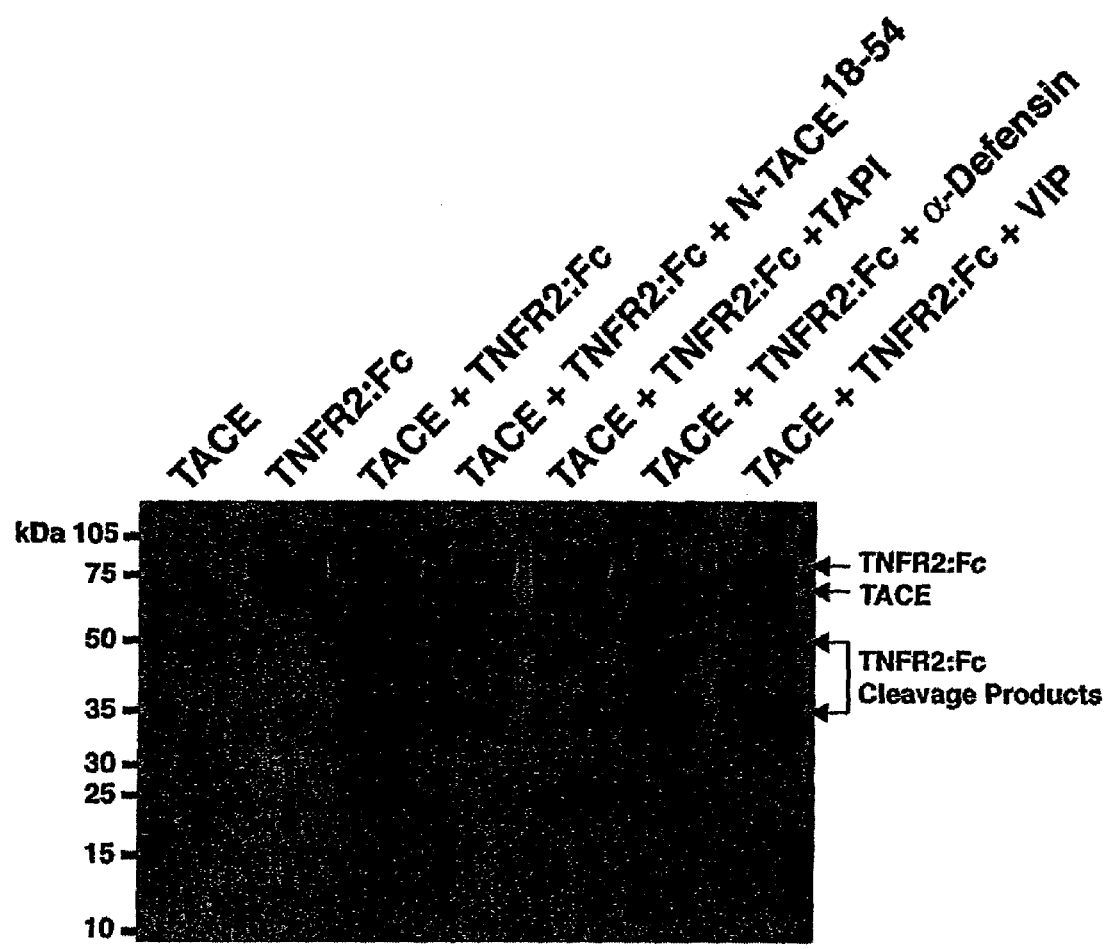
FIG. 4 shows that irrelevant peptides do not inhibit TACE-mediated cleavage of TNFR2. rhTACE (0.5 µM) was incubated with TNFR2:Fc (0.95 µM) alone, or in combination with N-TACE(18-54) (80 µM), TAPI-2 (25 µM), α-defensin (80 µM), or vasoactive intestinal peptide (VIP) (80 µM) for 30 min. Samples were then subjected to SDS-PAGE and visualized by silver staining. The position of TNFR2:Fc, TACE, and TNFR2:Fc cleavage products are indicated by arrows. Molecular weight markers are indicated on the left.

The irrelevant peptides, α-defensin and vasoactive intestinal peptide (VIP), were purchased from Bachem (Torrance, Calif.), and used to assess the specificity of N-TACE to inhibit TACE-mediated TNFR2. As shown in FIG. 4, neither α-defensin or VIP inhibited the ability of TACE to proteolytically cleave TNFR2:Fc. TACE-mediated TNFR2 cleavage was partially inhibited by 80 μM N-TACE(18-54) and completely inhibited by the hydroxamic acid zinc metalloprotease inhibitor, 25 μM TAPI-2 (purchased from Peptides International, Louisville, Ky.). These results indicate that the ability of N-TACE to inhibit TACE proteolytic activity is not a non-specific peptide effect.

Figure 5:
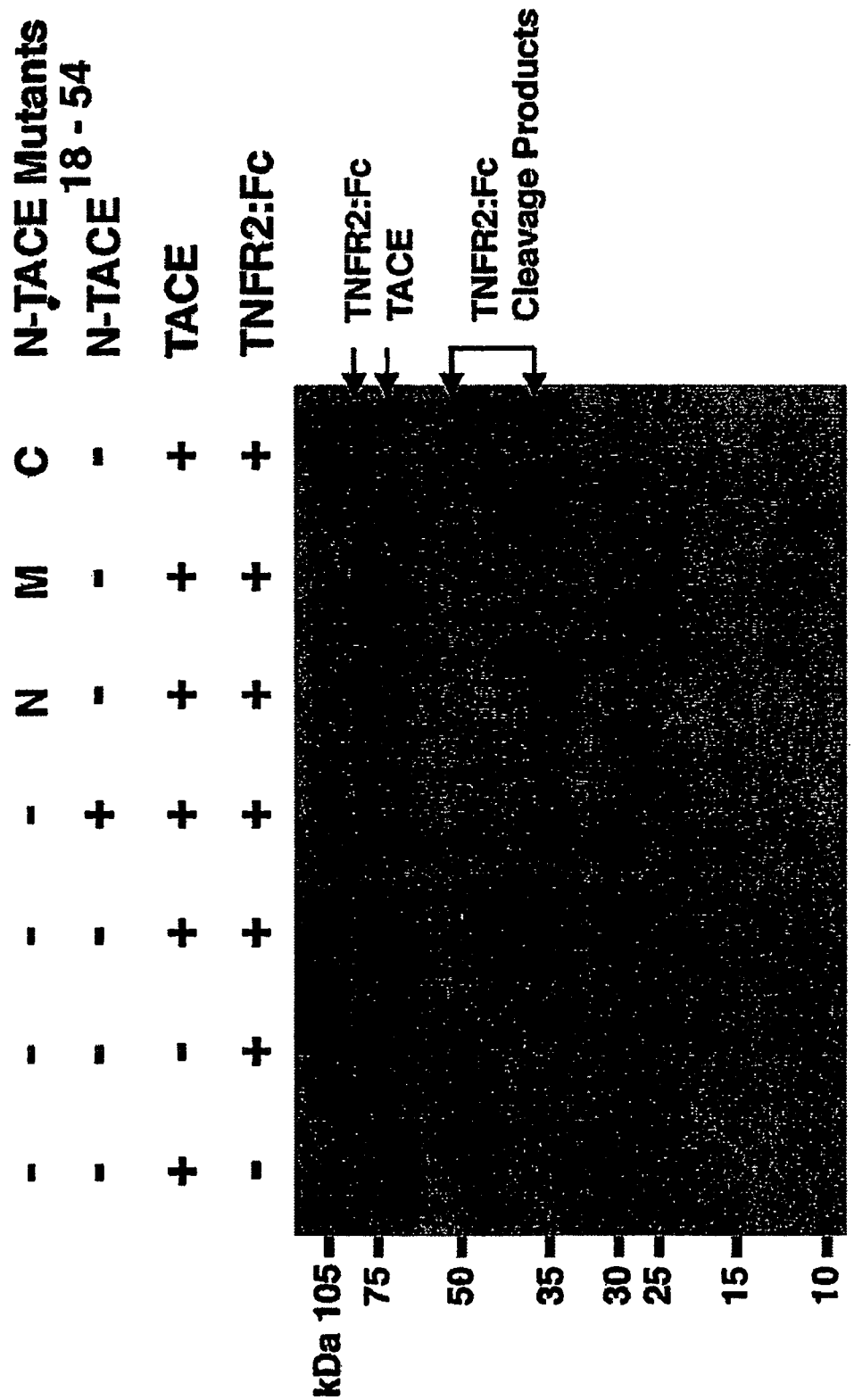
FIG. 5 shows the effect of N-TACE truncation mutants on TACE-mediated TNFR2 cleavage. rhTACE (0.5 µM) was incubated with TNFR2:Fc (0.95 µM) alone, or in combination with N-TACE (80 µM), N-TACE(18-29) (80 µM), N-TACE(30-42) (80 µM), or N-TACE(43-54) (80 µM), for 30 minutes. Samples were then subjected to SDS-PAGE and visualized by silver staining. The position of TNFR2:Fc, TACE, and TNFR2:Fc cleavage products are indicated by arrows. Molecular weight markers are indicated on the left. N: represents N-TACE(18-29), M: represents N-TACE(30-42), C: represents N-TACE(43-54).

The ability of different N-TACE domains to mediate TACE inhibitory activity was assessed using N-TACE(18-29), N-TACE(30-42), and N-TACE(43-54). As shown in FIG. 5, none of the N-TACE truncation mutants (80 μM) inhibited the ability of TACE to proteolytically cleave TNFR2:Fc. These results demonstrate that these N-TACE truncation mutants either have reduced TACE inhibitory activity, or do not possess TACE inhibitory activity. Further, because the N-TACE truncation mutants were synthesized in an identical fashion to full-length N-TACE, these results demonstrate that the ability of N-TACE to function as a TACE inhibitor is not an artifact related to its synthesis and purification.

Figure 6:
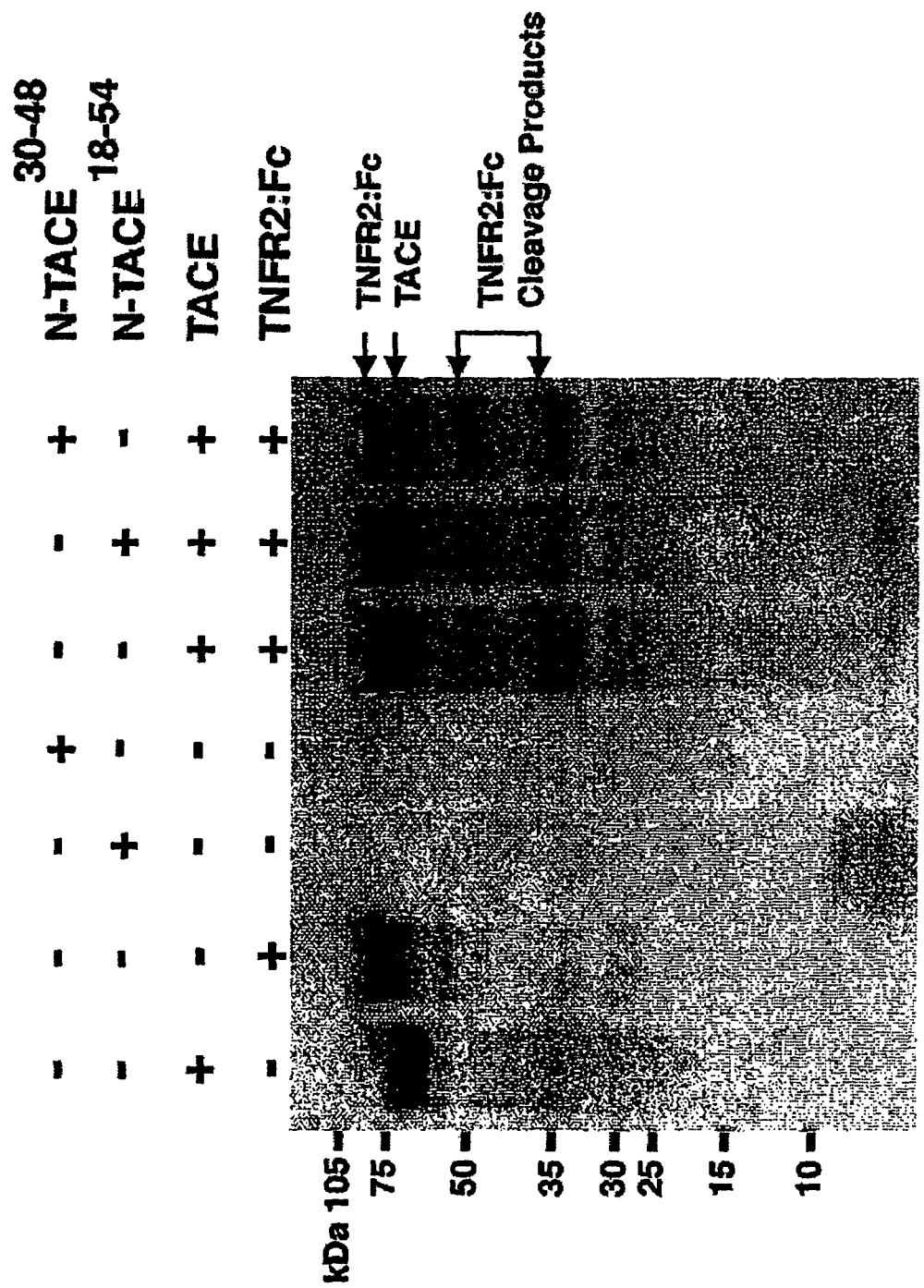
FIG. 6 illustrates the effect of N-TACE(30-48) on TACE-mediated TNFR2 cleavage. rhTACE (0.5 µM) was incubated with TNFR2:Fc (0.95 µM) alone, or in combination with N-TACE(18-54) (80 µM) or N-TACE(30-48) (80 µM) for 30 minutes. Samples were then subjected to SDS-PAGE and visualized by silver staining. The position of TNFR2:Fc, TACE, and TNFR2:Fc cleavage products are indicated by arrows. Molecular weight markers are indicated on the left.

The ability of a peptide corresponding to amino acids 30-48 of N-TACE (N-TACE(30-48)) to inhibit TACE was also tested. N-TACE(30-48) was predicted to have a helical structure by Chou Fasman analysis and is leucine-rich, which may be important for its ability to inhibit TACE activity. As shown in FIG. 6, both N-TACE(18-54) and N-TACE(30-48) inhibited the TACE-mediated proteolytic cleavage of TNFR2:Fc. These results demonstrate that a functional inhibitory peptide corresponds to amino acids 30-48 of N-TACE.

Figure 8:
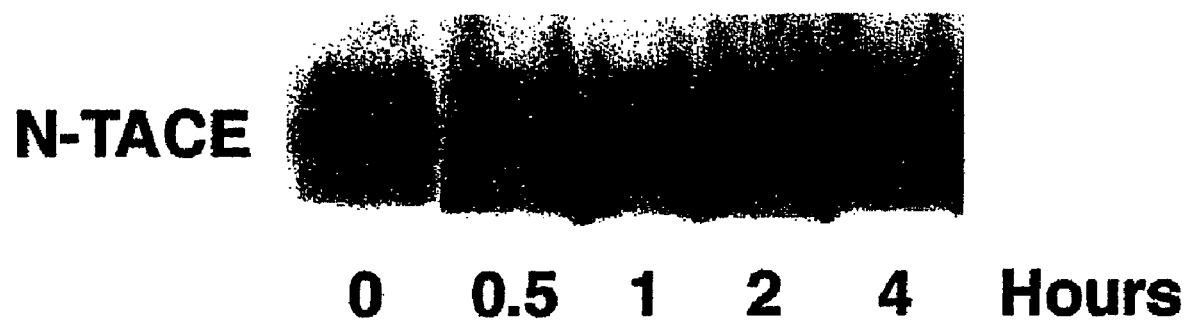
FIG. 8 shows that N-TACE is not degraded by TACE. N-TACE(18-54) (80 µM) was incubated with rhTACE (0.5 µM) for 30 minutes. Samples were separated by SDS-PAGE, transferred to nitrocellulose, and reacted with a polyclonal antibody that detects N-TACE(18-54).

The ability of TACE to degrade N-TACE was assessed. As shown by Western blotting in FIG. 8, there was no decrease in the quantity of N-TACE(18-54) following incubation with TACE for 4 hrs. These data indicate that N-TACE(18-54) is not a substrate for TACE.

Example III

Quantification of TNFR2 Shedding

The ability of N-TACE to inhibit TNFR2 shedding was tested in a cell-based system. U937 cells were obtained from ATCC (Manassas, Va.) and maintained in RPMI-1640 medium with 10% fetal bovine serum. For experiments, U937 cells were plated into 6 well plates at a density of $2 \times 10^6$ cells/ml. PMA was purchased from Sigma (St. Louis, Mo.). Release of TNFR2 into HUVEC cell culture supernatants over a 24-hour period was assayed utilizing a sandwich ELISA with a sensitivity of 7.8 pg/ml (R & D Systems). Cellular apoptosis and necrosis were measured using the TACS Annexin V-FITC Apoptosis Detection Kit (R & D Systems, Minneapolis, Minn.) and a XL-MCL Flow Cytometer (Becman-Coulter, Miami, Fla.). Statistical analysis was performed by a paired Student's t test with a Bonferroni correction for multiple comparisons and by single factor ANOVA. Differences were considered significant at a P value <0.05.

Figure 7:
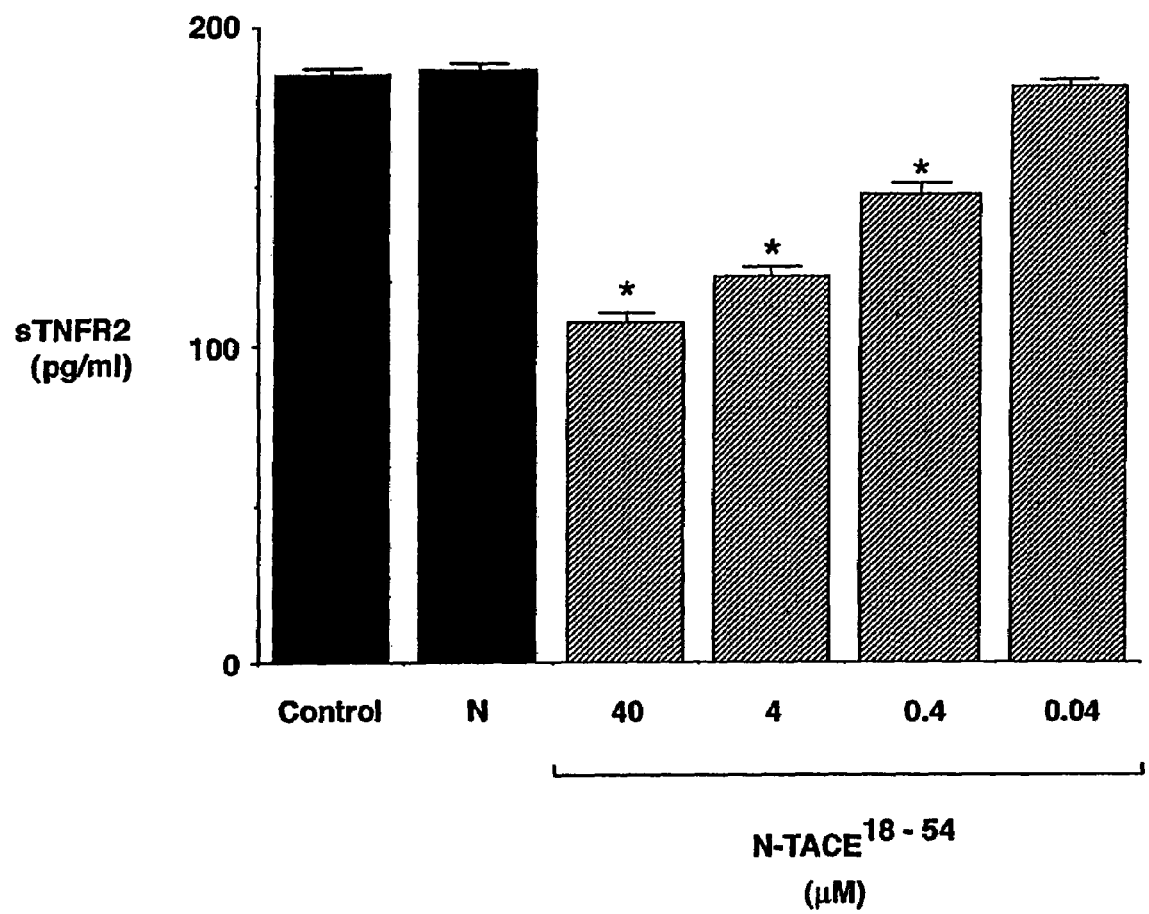
FIG. 7 illustrates the effect of N-TACE on TNFR2 shedding from U937 cells. U937 cells were treated for 24 hours with N-TACE(18-54) (0.04 to 40 µM), or with N-TACE(18-29) as a control. Soluble TNFR2 (sTNFR2) in cell culture supernatants was quantified by enzyme linked immunosorbent assay (ELISA) and compared to that in supernatants from untreated cells (n=6). N-TACE(18-54) inhibited TNFR2 shedding in a dose responsive fashion ($P<10^{-15}$ as compared to control, single factor ANOVA). * $P<0.05$ vs. untreated cells (control).

The U937 monocytic cells were treated for 24 hours with either N-TACE(18-54) (0.04 to 40 μM), or a peptide corresponding to N-TACE amino acids 18-29 (40 μM). As shown in FIG. 7, the quantity of soluble TNFR2 present in supernatants from cells treated with N-TACE(18-54) was significantly reduced in a dose-responsive fashion. Further, 40 μM N-TACE(18-54) significantly inhibited TNFR2 shedding by 42% as compared to cells treated with media alone (107.3±3.3 pg/ml vs. 184.6±2.2 pg/ml, P<10-8). In contrast, N-TACE(18-29) had no effect on TNFR2 shedding as compared to cells treated with media alone (186.5±1.8 vs. 184.6±2.2, n=6, P=NS). The ability of N-TACE(18-54) to decrease TNFR2 shedding was not a consequence of either apoptosis or necrosis, as assessed by Annexin V binding and propidium iodide uptake. These data indicate that N-TACE (18-54) significantly inhibits cell-associated TACE activity.

The ability of N-TACE(30-48) to inhibit TNFR2 shedding from U937 cells was also assessed. Treatment with 40 μM N-TACE(30-48) inhibited TNFR2 shedding by about 16% as compared to cells treated with media alone (160.8±3.4 vs. 190.4±2.9 pg/ml, n=6, P<$10^{-4}$). This indicates that peptides having an amino acid sequence that corresponds to a portion of N-TACE possess TACE inhibitory activity.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

50

What is claimed:

1. An isolated peptide consisting of any one of SEQ ID NOs: 3-8 or a fragment thereof that inhibits tumor necrosis factor alpha converting enzyme protease activity, wherein the fragment comprises any one of SEQ ID NO:4, 7 or 8.

2. The isolated peptide of claim 1, consisting essentially of SEQ ID NO:3.

3. The isolated peptide of claim 1, wherein the peptide includes an amino-terminal blocker, a carboxyl-terminal blocker, or both an amino-terminal blocker and a carboxyl-terminal blocker.

4. The isolated peptide of claim 1, wherein the isolated peptide is coupled to a partner protein.

5. The isolated peptide of claim 4, wherein the isolated peptide is chemically coupled to the partner protein.

6. The isolated peptide of claim 4, wherein the partner protein is a carrier protein.

7. The isolated peptide of claim 6, wherein the carrier protein is keyhole limpet hemacyanin, bovine serum albumin, ovalbumin, mouse serum albumin, rabbit serum albumin.

8. The isolated peptide of claim 4, wherein protein does not include an amino acid sequence PKVCGY (SEQ ID NO:2) or PKTCGY (SEQ ID NO:9).

9. The isolated peptide of claim 4, wherein the partner protein is avidin, biotin, an antibody epitope, poly histidine, glutathione-S-transferase, an export signal peptide, or maltose binding protein.

10. A pharmaceutical composition comprising a pharmaceutically acceptable carrier and the isolated peptide of claim 1.

11. A polyprotein comprising at least two of the isolated peptides of claim 1 connected by one or more linkers.

12. The polyprotein of claim 11, wherein the one or more linkers are cleavable with a chemical or a protease.

13. The polyprotein of claim 11, wherein the polyprotein is connected to a partner protein by a separate linker.

14. The polyprotein of claim 13, wherein the separate linker is cleavable with a chemical or a protease.

15. An isolated peptide consisting of any one of SEQ ID NO:3 or a fragment thereof that inhibits tumor necrosis factor alpha converting enzyme protease activity, wherein the fragment comprises SEQ ID NO: 4.

16. An isolated peptide consisting of SEQ ID NO:7 or SEQ ID NO:4.

17. An isolated peptide consisting of any one of SEQ ID NO: 8 or a fragment thereof that inhibits tumor necrosis factor alpha converting enzyme protease activity, wherein the fragment comprises SEQ ID NO:4.

18. A method to lower levels of active tumor necrosis factor alpha in a mammal in need thereof comprising administering to the mammal a tumor necrosis factor alpha lowering amount of the peptide of claim 1.

* * * * *

UNITED STATES PATENT AND TRADEMARK OFFICE
CERTIFICATE OF CORRECTION

| | | |
|---|---|---|
| PATENT NO. | : 7,655,752 B2 | Page 1 of 1 |
| APPLICATION NO. | : 11/389675 | |
| DATED | : February 2, 2010 | |
| INVENTOR(S) | : Levine et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 396 days.

Signed and Sealed this

Twenty-third Day of November, 2010

David J. Kappos
*Director of the United States Patent and Trademark Office*